(12) United States Patent
Rossignol et al.

(10) Patent No.: US 6,683,063 B2
(45) Date of Patent: *Jan. 27, 2004

(54) PREVENTION AND TREATMENT OF PULMONARY BACTERIAL INFECTION OR SYMPTOMATIC PULMONARY EXPOSURE TO ENDOTOXIN BY INHALATION OF ANTIENDOTOXIN DRUGS

(75) Inventors: Daniel P. Rossignol, Mahwah, NJ (US); Mary W. Vermeulen, Ipswich, MA (US)

(73) Assignee: Eisai Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/167,222

(22) Filed: Jun. 11, 2002

(65) Prior Publication Data

US 2003/0134805 A1 Jul. 17, 2003

Related U.S. Application Data

(63) Continuation of application No. 09/449,601, filed on Nov. 23, 1999, now Pat. No. 6,417,172, which is a continuation-in-part of application No. 09/293,856, filed on Apr. 16, 1999, now Pat. No. 6,184,366, which is a continuation of application No. 08/658,656, filed on Jun. 5, 1996, now Pat. No. 5,935,938, which is a continuation-in-part of application No. 08/461,675, filed on Jun. 5, 1995, now Pat. No. 5,750,664.

(51) Int. Cl.[7] .............................................. A61K 31/70
(52) U.S. Cl. ...................... 514/53; 536/17.2; 536/17.9; 536/123.13
(58) Field of Search ........................... 514/53; 536/17.2, 536/17.9, 123.13

(56) References Cited

U.S. PATENT DOCUMENTS

| 5,066,794 | A |   | 11/1991 | Shiba et al. |
| 5,530,113 | A |   | 6/1996  | Christ et al. |
| 5,750,664 | A | * | 5/1998  | Christ et al. ............... 536/17.2 |
| 5,935,938 | A | * | 8/1999  | Christ et al. .................. 514/53 |
| 6,184,366 | B1| * | 2/2001  | Christ et al. ............... 536/17.2 |
| 6,417,172 | B1|   | 7/2002  | Rossignol et al. |

FOREIGN PATENT DOCUMENTS

| EP | 0 172 581 | 2/1986 |
| EP | 0 536 969 | 4/1993 |
| WO | 96 39411  | 12/1996 |

OTHER PUBLICATIONS

Van Rozendaal et al., "Aerosolized Endotoxin is Immediately Bound by Pulmonary Surfactant Protein D in vivo," Biochimica et Biophysica Acta 1454:261–269, 1999.

* cited by examiner

*Primary Examiner*—Elli Peselev
(74) *Attorney, Agent, or Firm*—Clark & Elbing LLP

(57) ABSTRACT

The invention provides methods of preventing and treating pulmonary bacterial infection or symptomatic pulmonary exposure to endotoxin and related conditions in a patient by administering to the patient antiendotoxin compounds by inhalation.

4 Claims, 3 Drawing Sheets

PREVENTION AND TREATMENT OF PULMONARY BACTERIAL INFECTION OR SYMPTOMATIC PULMONARY EXPOSURE TO ENDOTOXIN BY INHALATION OF ANTIENDOTOXIN DRUGS

CROSS REFERENCE TO RELATED APPLICATIONS

This application is a continuation of and claims priority from U.S. patent application Ser. No. 09/449,601, filed Nov. 23, 1999 (now U.S. Pat. No. 6,417,172), which is a continuation-in-part of U.S. patent application Ser. No. 09/293,856, filed Apr. 16, 1999 (now U.S. Pat. No. 6,184,366), which is a continuation of U.S. patent application Ser. No. 08/658,656, filed Jun. 5, 1996 (now U.S. Pat. No. 5,935,938), which is a continuation-in-part of U.S. patent application Ser. No. 08/461,675, filed Jun. 5, 1995 (now U.S. Pat. No. 5,750,664).

FIELD OF INVENTION

This invention relates to methods that are useful in the prophylactic and affirmative treatment of pulmonary bacterial infection or symptomatic pulmonary exposure to endotoxin by inhalation of antiendotoxin compounds.

BACKGROUND OF THE INVENTION

The incidence of gram-negative bacteremia in the United States has been estimated to be approximately 100,000 to 300,000 cases per year, with a mortality rate of 30–60%. Antibiotics are commonly used as the primary chemotherapy for this disease; however, their bactericidal action can result in disruption of the bacterium and concomitant release of endotoxin, i.e., the lipopolysaccharide (LPS) moiety of the bacterial outer membrane. The liberated LPS induces a number of pathophysiological events in mammals (collectively referred to as gram-negative endotoxemia or sepsis syndrome). These include fever, generalized inflammation, disseminated intravascular coagulation (DIC), hypotension, acute renal failure, acute respiratory distress syndrome (ARDS), hepatocellular destruction, and cardiac failure.

Although endotoxin initiates septic shock, it has little or no direct toxic effect on tissues; instead, it triggers an immunobiological response leading to a cascade of release of cytokines, such as tumor-necrosis factor (TNF), interleukin-1, interleukin-6, and interleukin-8, and other biological mediators, such as nitric oxide, as well as an array of secondary mediators (e.g., prostaglandins, leukotrienes, interferons, platelet-activating factor, endorphins, and colony-stimulating factors). Generation of pathophysiological concentrations of these cytokines and inflammatory mediators influences vasomotor tone, microvascular permeability, and the aggregation of leukocytes and platelets, causing a syndrome termed "systemic inflammatory response syndrome" (or SIRS) and septic shock.

The bacterial lipopolysaccharide molecule has three main regions: a long chain polysaccharide (O Antigen), a core region, and a Lipid A region. The entire lipopolysaccharide molecule, as well as some of its individual components, possess toxic effects, as is described above. Most of these toxic effects, however, are believed to be attributable to the Lipid A portion. Structurally, Lipid A is composed of a diphosphorylated disaccharide, acylated by long chain fatty acids.

Therapies for endotoxin-related diseases have generally been directed towards controlling the inflammatory response. Such therapies include corticosteriod treatment, suggested to ameliorate endotoxin-mediated cell membrane injury and to reduce production of certain biological mediators; administration of antibodies designed to neutralize bacterial LPS; treatment with agents to suppress hypotension or with naloxone, which apparently blocks the hypotensive effects associated with sepsis syndrome; and treatment with nonsteroidal anti-inflammatory drugs, purported to block cyclooxygenanses and, thereby, decrease the production of certain secondary mediators, such as prostaglandins and thromboxane.

However, none of these therapies to date has resulted in significant reduction in the morbidity and mortality resulting from sepsis and septic shock syndrome. Thus, there is a long felt need for agents to affirmatively treat this disorder.

Christ et al., "Anti-Endotoxin Compounds," U.S. Pat. No. 5,530,113, the contents of which are included by reference, disclose certain disaccharide compounds, such as B531, shown below, useful for the treatment of endotoxemia.

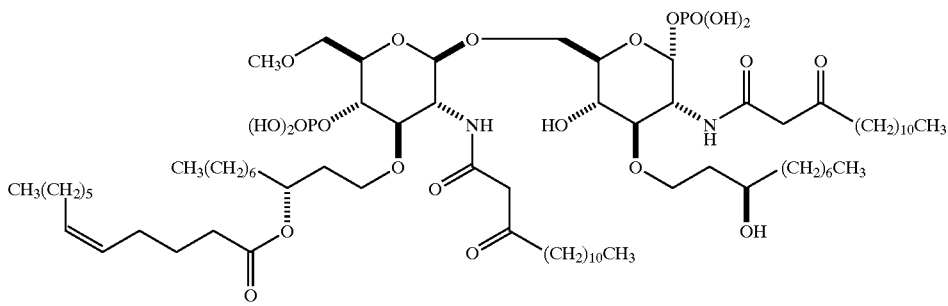

B531

Other references that disclose certain lipodisaccharides include Macher et al., Great Britain Patent No. 2,179, 945; Meyers et al., Great Britain Patent No. 2,220,211; Shiba et al., European Patent No. 172,581; Anderson et al., U.S. Pat. No. 4,495,346; and Shiba et al., U.S. Pat. No. 5,066,794.

SUMMARY OF THE INVENTION

The present invention is directed to the prevention and treatment of pulmonary bacterial infection or symptomatic pulmonary exposure to endotoxins and related disorders using liposaccharide analogs that are administered by inhalation. The compounds used in the present invention possess advantages for pharmaceutical use, such as enhanced pharmacological selectivity, efficacy, and, in particular, increased persistence of action. A representative compound of this invention, compound 1 (1287, SGEA), is shown below:

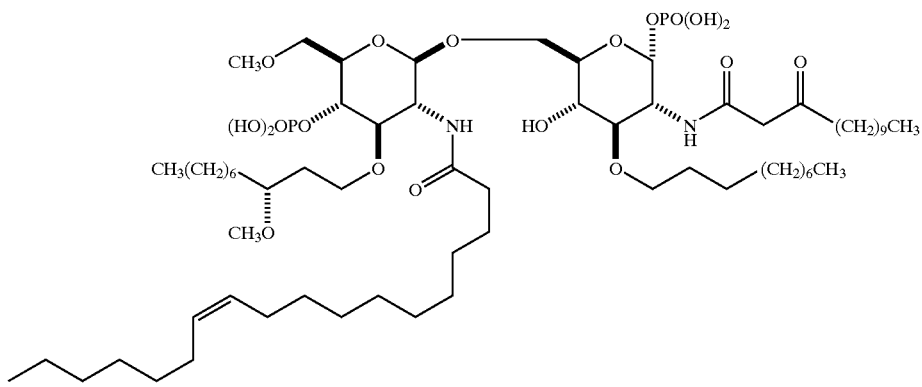

Compound 1

Further, the present invention is directed to the prophylactic and affirmative treatment of any LPS-mediated disorder. These disorders include, but are not limited to, sepsis, septicemia (including but not limited to endotoxemia), endotoxemia resulting from gram-negative bacteremia (with its accompanying symptoms of fever, generalized inflammation, disseminated intravascular coagulation, hypotension, acute renal failure, acute respiratory distress syndrome, adult respiratory distress syndrome (ARDS), hepatocellular destruction and/or cardiac failure) and various forms of septic shock (including but not limited to endotoxic shock). Also, compounds of this invention will be useful in the prophylactic or affirmative treatment of localized or systemic inflammatory response to infection by different types of organisms, including gram-negative bacteria, and in diseases related to translocation of gram-negative bacteria or endotoxin from the gut. Together, these disorders are termed systemic inflammatory response syndrome or SIRS. (For a discussion of these terms, see Bone et al., Chest 101:1644–1655, 1992.)

Definitions

In accordance with the present invention and as used herein, the following terms are defined with the following meanings, unless explicitly stated otherwise.

The term "alkyl" refers to aliphatic organic groups that may be branched or straight and which may be optionally substituted with one or more halogen atoms at any position along the alkyl chain. Alkyl groups include both groups that have a single unoccupied valence, for example, —CH$_2$—CH$_3$, and alkylene groups, which have two unoccupied valences, for example —CH$_2$—CH$_2$—. As is obvious to those skilled in the art, the single or double unoccupied valence will be used as appropriate to describe compounds that are chemically stable.

The term "prodrug" as used herein refers to any compound that has less intrinsic activity than the corresponding "drug," but when administered to a biological system, generates the "drug" substance, either as a result of spontaneous chemical reaction or by enzyme catalyzed or metabolic reaction. Reference is made to various prodrugs, such as acyl esters, carbonates, phosphates, and urethanes, included herein as examples. The groups illustrated are exemplary, not exhaustive, and one skilled in the art could prepare other known varieties of prodrugs. Such prodrugs of the compounds of Formula I fall within the scope of the present invention.

The term "pharmaceutically acceptable salt" includes salts of compounds of Formula I derived from the combination of a compound of this invention and an organic or inorganic acid or base. The compounds of Formula I are useful in both non-ionized and salt form. In practice, the use of a salt form amounts to use of a base form; both forms are within the scope of the invention.

The term "geometric isomers" refers to "trans" or "cis" (or "entgegen" or "zusammen") isomers, as generally understood by those skilled in the art. All geometric isomers are within the scope of the invention.

Further, compounds of the present invention may contain asymmetric carbon atoms, and hence can exist as stereoisomers, both enantiomers and diastereomers. All stereoisomers and mixtures thereof are considered to fall within the scope of the present invention. The synthetic examples cited herein provide the most preferred isomer. It is evident that, in addition to the sugar moiety, additional asymmetric carbons may be present in compounds of Formula I, for example, in the side chains. In this event, all of the resulting diastereomers are considered to fall within the scope of the present invention.

DETAILED DESCRIPTION

Figure 1:
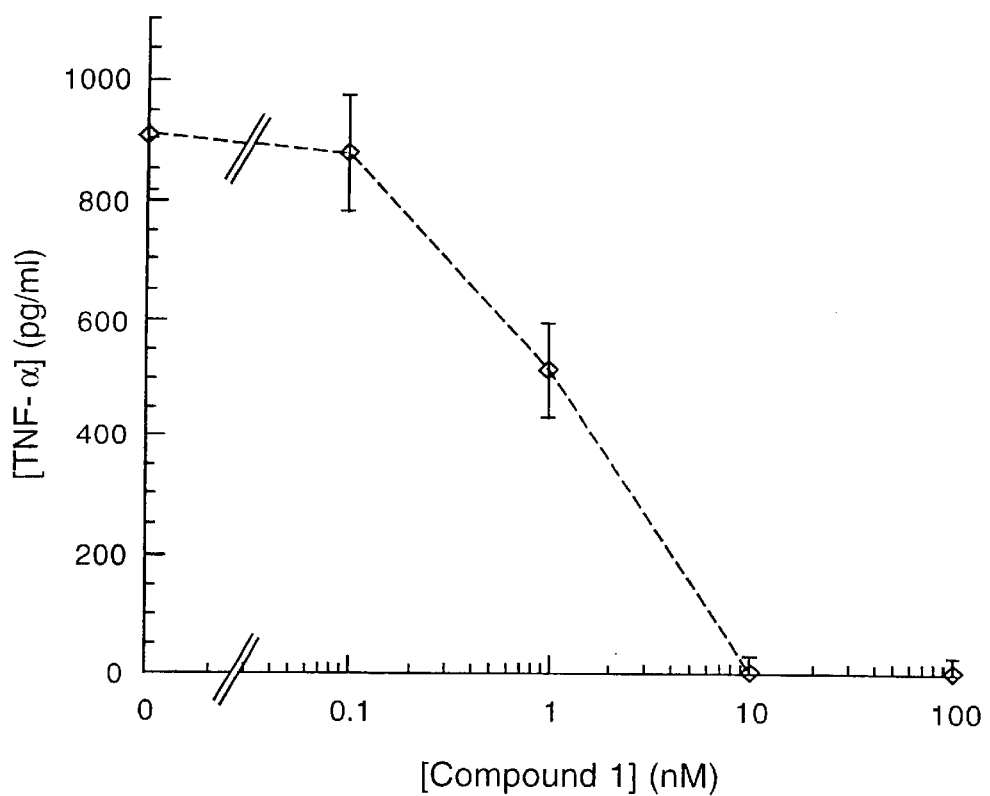
FIG. 1 depicts the inhibition of release of TNF-α by Compound 1 illustrating the inhibition of LPS-mediated induction of tumor necrosis factor (TNF) in human whole blood by a compound of this invention.

The invention provides methods of preventing and treating pulmonary bacterial infection, symptomatic pulmonary exposure to endotoxin, and related conditions in a patient by administering to the patient an antiendotoxin compound by inhalation. These compounds and methods are described further, as follows.

Liposaccharides

In one aspect, the present invention relates to the use of substituted liposaccharides that include compounds of the general formula I.

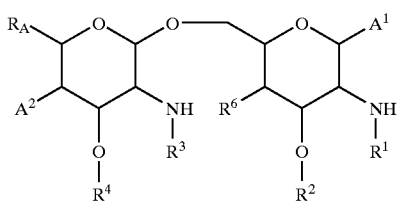

where $R^1$ is selected from the group consisting of

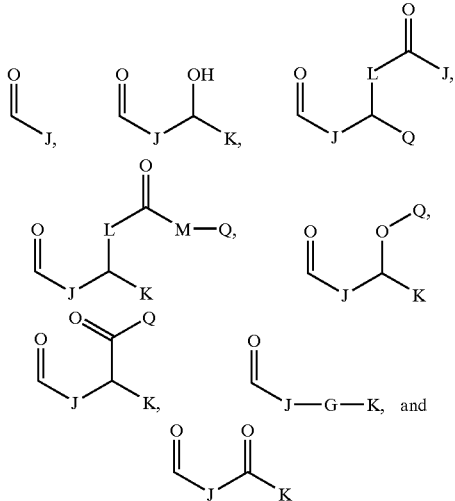

where each J, K, and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;
$R^3$ is selected from the group consisting of straight or branched C5 to C18 alkyl,

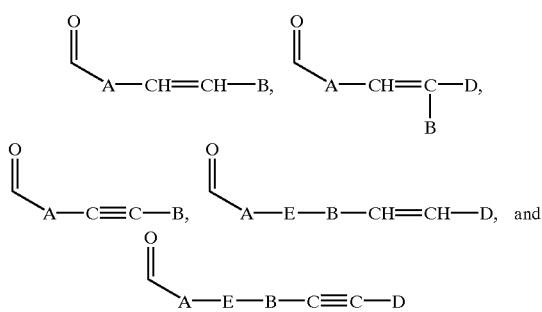

where E is NH, O, S, SO, or $SO_2$; each A, B, and D, independently, is straight or branched C1 to C15 alkyl;
$R^4$ is selected from the group consisting of straight or branched C4 to C20 alkyl, and

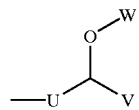

where each U and V, independently, is straight or branched C2 to C15 alkyl and W is hydrogen or straight or branched C1 to C5 alkyl;
$R_A$ is $R^5$ or $R^5$—O—$CH_2$—, $R^5$ being selected from the group consisting of hydrogen, J',—J'—OH, —J'—O—K',—J'—O—K'—OH, and —J'—O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;
$A^1$ and $A^2$, independently, are selected from the group consisting of

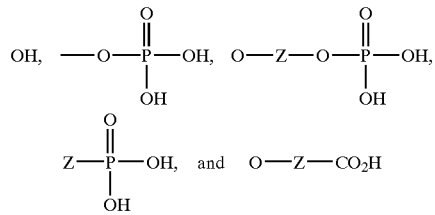

where Z is straight or branched C1 to C10 alkyl; or pharmaceutically acceptable salts thereof.

Embodiments of the above formula include the following or combinations of the following:

$R^2$ is C8 to C15 straight or branched alkyl;
$R^2$ is C9 to C12 straight or branched alkyl;
$R^2$ is C10 straight or branched alkyl;
$A^1$ and $A^2$, independently, are OH or —O—PO(OH)$_2$;
$R^6$ is hydroxy;
$R^5$ is C1 to C5 straight or branched alkyl;
$R^1$ is selected from the group consisting of

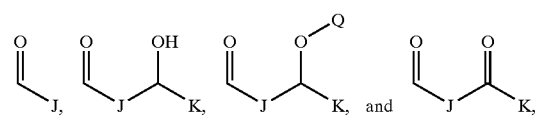

where each J, K, and Q, independently, is straight or branched C1 to C15 alkyl;
$R^3$ is selected from the group consisting of

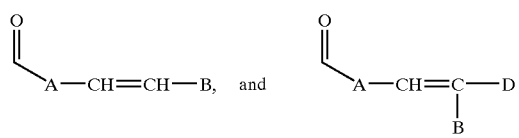

where each A, B, and D, independently, is straight or branched C1 to C18 alkyl;
the double bonds of $R^3$ are cis or zusammen;
the double bonds of $R^3$ are trans or entgegen;
$R^4$ is selected from the group consisting of straight or branched C4 to C20 alkyl, and

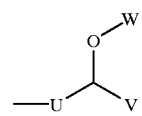

where U is straight or branched C2 to C5 alkyl, V is straight or branched C5 to C12 alkyl, and W is hydrogen or straight or branched C1 to C5 alkyl;
$R_A$ is $R^5$; and $R_A$ is $R^5$—O—CH2—.

In other embodiments, each $A^1$ and $A^2$, independently, is selected from the group consisting of OH and —O—PO(OH)$_2$;

$R^1$ is selected from the group consisting of

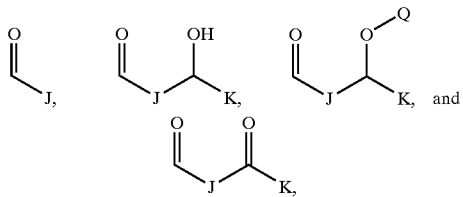

where each J, K, and Q, independently, is straight or branched C1 to C15 alkyl;

$R^2$ is straight or branched C8 to C15 alkyl;

$R^3$ is selected from the group consisting of

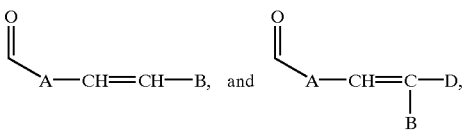

where each A, B, and D, independently, is straight or branched C1 to C15 alkyl;

$R^4$ is

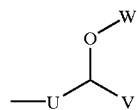

where U is straight or branched C2 to C5 alkyl, V is straight or branched C5 to C12 alkyl and W is hydrogen or straight or branched C1 to C5 alkyl;

and $R^5$ is straight or branched C1 to C5 alkyl; and $R^6$ is hydroxy.

In another embodiment, $A^1$ and $A^2$ are —O—PO(OH)$_2$;

$R^1$ is selected from the group consisting of

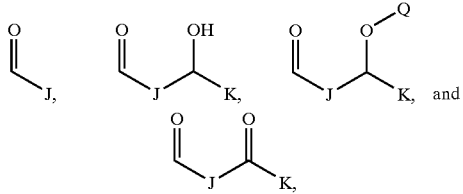

where each J and Q, independently, is straight or branched, C1 to C5 alkyl, and K is straight or branched C8 to C15 alkyl;

$R^2$ is straight or branched C8 to C15 alkyl;

$R^3$ is

where A is straight or branched C5 to C12 alkyl and B is straight or branched C6 to C12 alkyl;

$R^4$ is

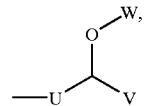

where U is straight or branched C2 to C5 alkyl, V is straight or branched C5 to C12 alkyl and W is hydrogen or straight or branched C1 to C5 alkyl; and $R^5$ is straight or branched C1 to C5 alkyl; and $R^6$ is hydroxy.

In another embodiment, $A^1$ and $A^2$ are —O—PO(OH)$_2$;

$R^1$ is selected from the group consisting of

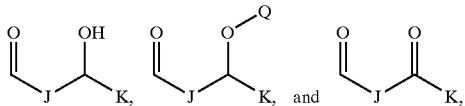

where each J and Q, independently, straight or branched is C1 to C3 alkyl, and K is straight or branched C10 to C12 alkyl;

$R^2$ is straight or branched C9 to C12 alkyl;

$R^3$ is

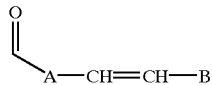

where A is straight or branched C8 to C12 alkyl and B is straight or branched C6 to C10 alkyl;

$R^4$ is

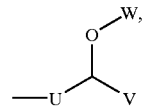

where U is straight or branched C2 to C4 alkyl, V is straight or branched C5 to C10 alkyl and W is hydrogen or straight or branched C1 to C3 alkyl; and $R^5$ is straight or branched C1 to C3 alkyl; and $R^6$ is hydroxy.

In another embodiment, $A^1$ and $A^2$ are —O—PO(OH)$_2$;

$R^1$ is

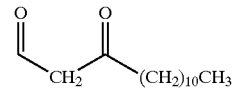

$R^2$ is (CH$_2$)$_9$CH$_3$;

$R^3$ is

$R^4$ is

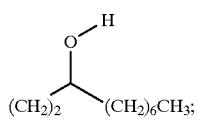

$R^5$ is —CH$_3$; and
$R^6$ is hydroxy.

Also within the scope of the invention are compounds in which R1 and R3 are sulfonyls, i.e., compounds in which the carbonyl on these side chains is replaced with SO$_2$. These compounds could be prepared by treating the appropriately substituted alcoholic sugar with the appropriate alkylsulfonyl chloride. Thus, R1 and R3 may also be selected from the following with A, B, D, E, J, K, L, Q, and M as defined above:

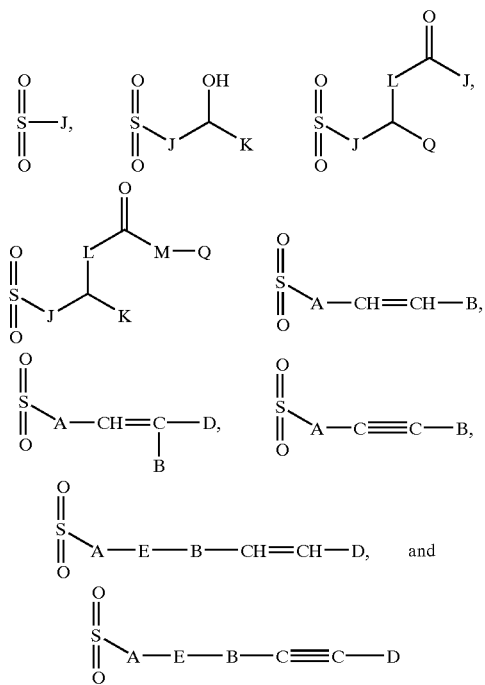

Further, within the scope of the invention are compounds in which the point of unsaturation within the R3 side chain is not a double or triple carbon—carbon bond but is an optionally substituted aromatic group, i.e., compounds in which R3 may have the following structure:

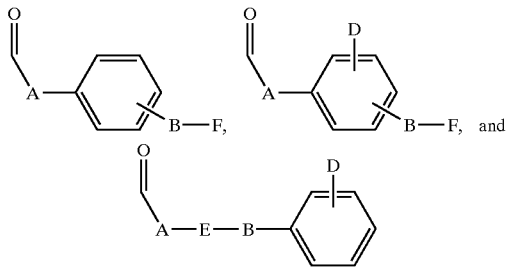

where E is NH, O, S, SO, or SO2; each A is straight or branched C1 to C15 alkylene; D is straight or branched C1 to C15 alkyl; F is H, —OT, NT$^1$T$^2$, —CO2T, phenyl or null wherein each of T, T$^1$, and T$^2$ is independently selected from hydrogen or C1 to C5 alkyl; where B is next to F and F is null, B is straight or branched C1 to C15 alkyl;

In general, preferred are compounds where:

$R^1$ is selected from the group consisting of:

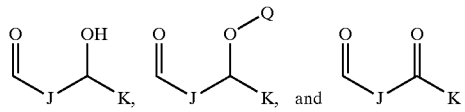

where each J, K, and Q independently, is straight or branched C1 to C15 alkyl;

$R^2$ is straight or branched C8 to C12 alkyl;

$R^3$ is selected from the group consisting of:

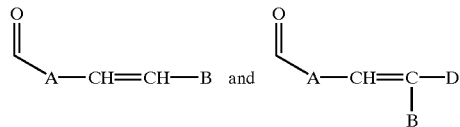

where each A, B, and D, independently, is straight or branched C1 to C15 alkyl;

$R^4$ is

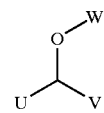

where U is straight or branched C2 to C5 alkyl, V is straight or branched C4 to C10 alkyl and W is hydrogen or straight or branched C1 to C5 alkyl;

$R^5$ is selected from the group consisting of: hydrogen, —J', and —J'OH where J' is C1 to C5 straight or branched alkyl;

$R^6$ is selected from the group consisting of hydroxy, halogen, and C1 to C5 acyloxy;

each A$^1$ and A$^2$, independently, are selected from the group consisting of:
OH and

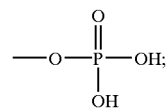

and pharmaceutically acceptable salts thereof.

Most preferred are compounds of formula 1 where:

$R^1$ is selected from the group consisting of:

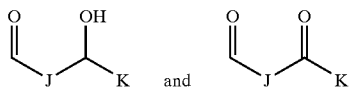

where J is straight or branched C1 to C5 alkyl and K is straight or branched C9 to C14 alkyl;

$R^2$ is straight or branched C8 to C12 alkyl;

R³ is

where A is straight or branched C6 to C12 alkyl and B is straight or branched C4 to C8 alkyl;

R⁴ is

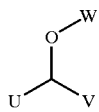

where U is straight or branched C2 to C4 alkyl, V is straight or branched C5 to C9 alkyl and W is hydrogen or straight or branched C1 to C3 alkyl;

R⁵ is C1 to C3 straight or branched alkyl;
R⁶ is hydroxy;
A¹ and A² are

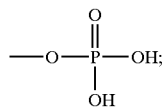

or pharmaceutically acceptable salts thereof.

General Synthetic Methods

This invention is also directed to processes for preparing compounds of Formula I. Disclosed herein are general synthetic routes for preparing variously substituted compounds of this invention. The synthesis for a compound of this invention, compound 1 (1287; SGEA), is shown below.

Most of the reagents and starting materials are well known to those skilled in the art. Certain reagents and starting materials for this preparation are described in detail by Christ et al., U.S. Pat. No. 5,530,113, the disclosure of which is hereby incorporated by reference.

One synthesis of the compounds of this invention is outlined below. Although this example describes the preparation of compound 1 (1287; SGEA), use of alternate starting materials will yield other analogs of this invention. Thus, the synthesis is indeed general in nature.

For example, use of alternative alkylating agents in synthetic step 22 will provide analogs with structurally differing substituents at R1. The substitution pattern at R2 is controlled by the use of the proper alkylating agent in step 15. Further, substitution of suitable alternative compounds in step 25 in the synthesis will produce analogs that differ with respect to R3.

Analogs without the oxygenated side chain at $R_A$ may be prepared by using slight variations in the synthetic scheme shown below, as is will known to those skilled in the art. For the compound in which $R_A$ is methyl, for example, the product of synthetic step 8, the tosylate, could have this leaving group replaced by iodine in the Finklestein reaction. The iodo compound could be dehalogenated by treatment with zinc metal to give a methyl group at position $R_A$.

A representative synthesis of the R4 side chain is outlined below. Preparation of variations of this side chain may be achieved by replacing the starting material with other suitable starting materials. For example, the length or branching of this side chain may be prepared by starting with the appropriate starting material. Thus the use of alternative tosylates in step 6 will produce variation in R4.

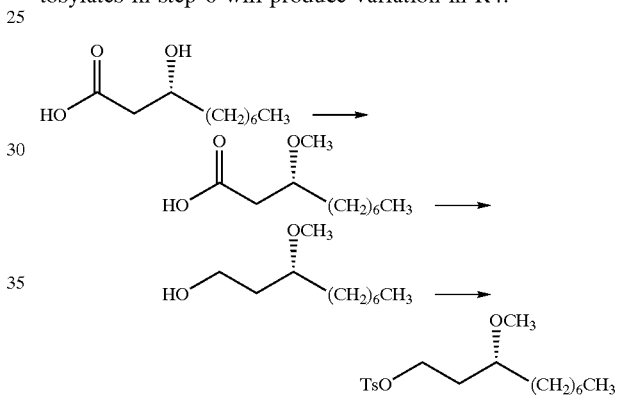

Thus the synthesis briefly outlined below provides versatile pathways to the compounds of this invention. (For details regarding the synthesis, see the following experimental examples.)

Compound 1 (as the sodium salt)

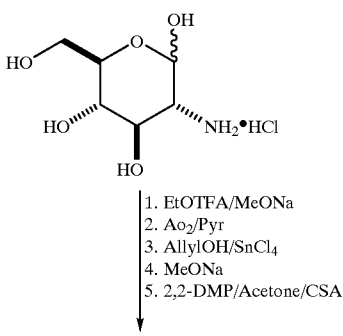

1. EtOTFA/MeONa
2. Ao₂/Pyr
3. AllylOH/SnCl₄
4. MeONa
5. 2,2-DMP/Acetone/CSA

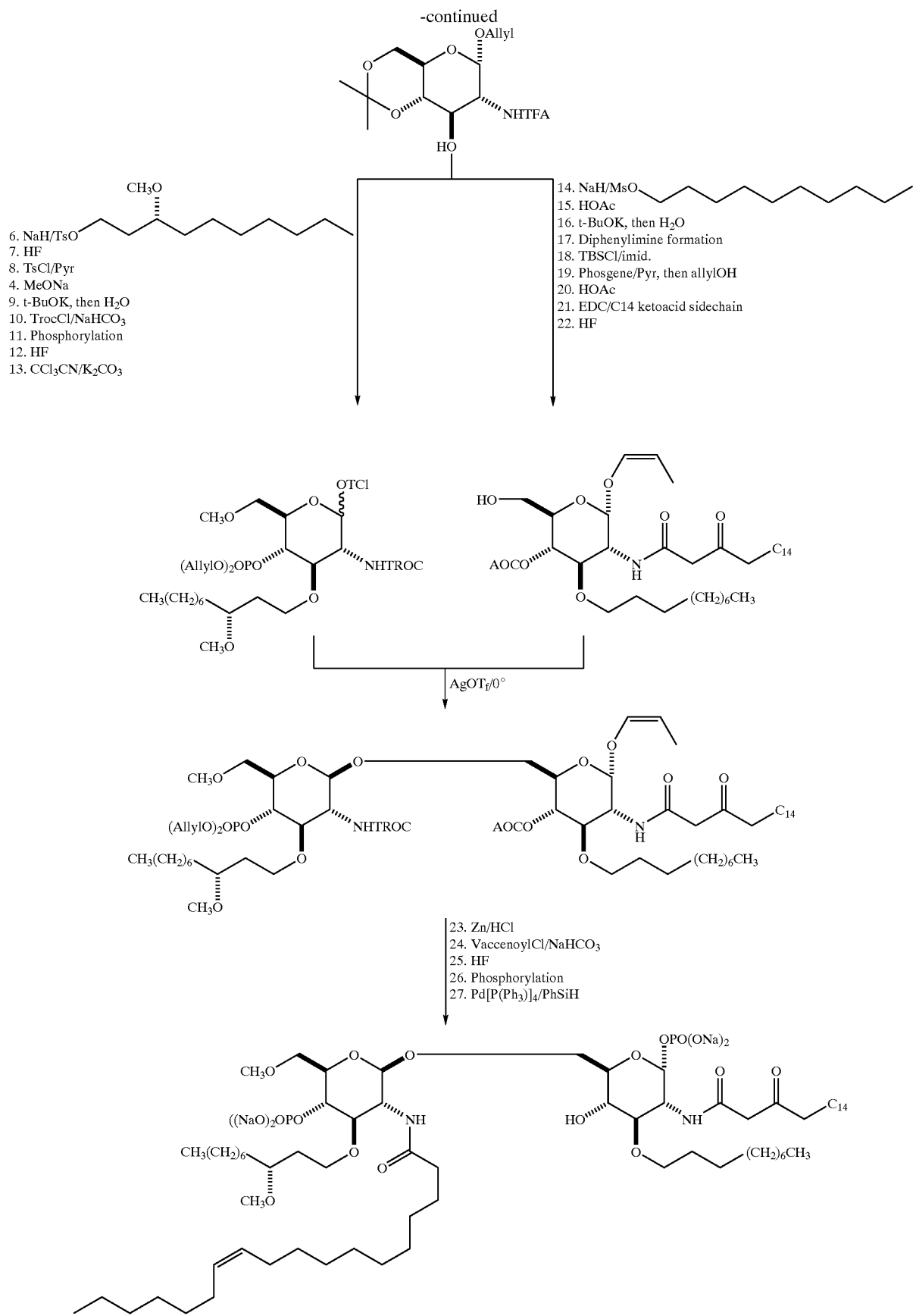

Applicants believe that the above-shown route, Route 1, is the superior method of preparing compounds of the present invention. Due to a variety of factors, such as use of cheaper starting materials, higher yields, and use of less toxic chemical agents, the route illustrated below, Route 2, may be used to prepare compounds of this invention.

Most of the reagents and starting materials are well known to those skilled in the art. Certain reagents and starting materials for this preparation are described in detail by Christ et al., U.S. Pat. No. 5,530,113, the disclosure of which is hereby incorporated by reference. Although this example describes the preparation of compound 1, use of alternate starting materials will yield other analogs of this invention. Thus the synthesis is indeed general in nature.

For example, use of alternative alkylating agents in the preparation of intermediate U will provide analogs with structurally differing substituents at R1. The substitution pattern at R2 is controlled by the use of the proper alkylating agent in the preparation of intermediate O. Further, substitution of suitable alternative compounds for intermediate E in the preparation of intermediate G will produce analogs which differ with respect to R3.

A representative synthesis of the R4 side chain is outlined below. Preparation of variations of this side chain may be achieved by replacing the starting material with other suitable starting materials. For example, the length or branching of this side chain may be prepared by starting with the appropriate starting material. (For details regarding the synthesis, see the following experimental examples.)

A representative preparation of the "left" portion is outlined below.

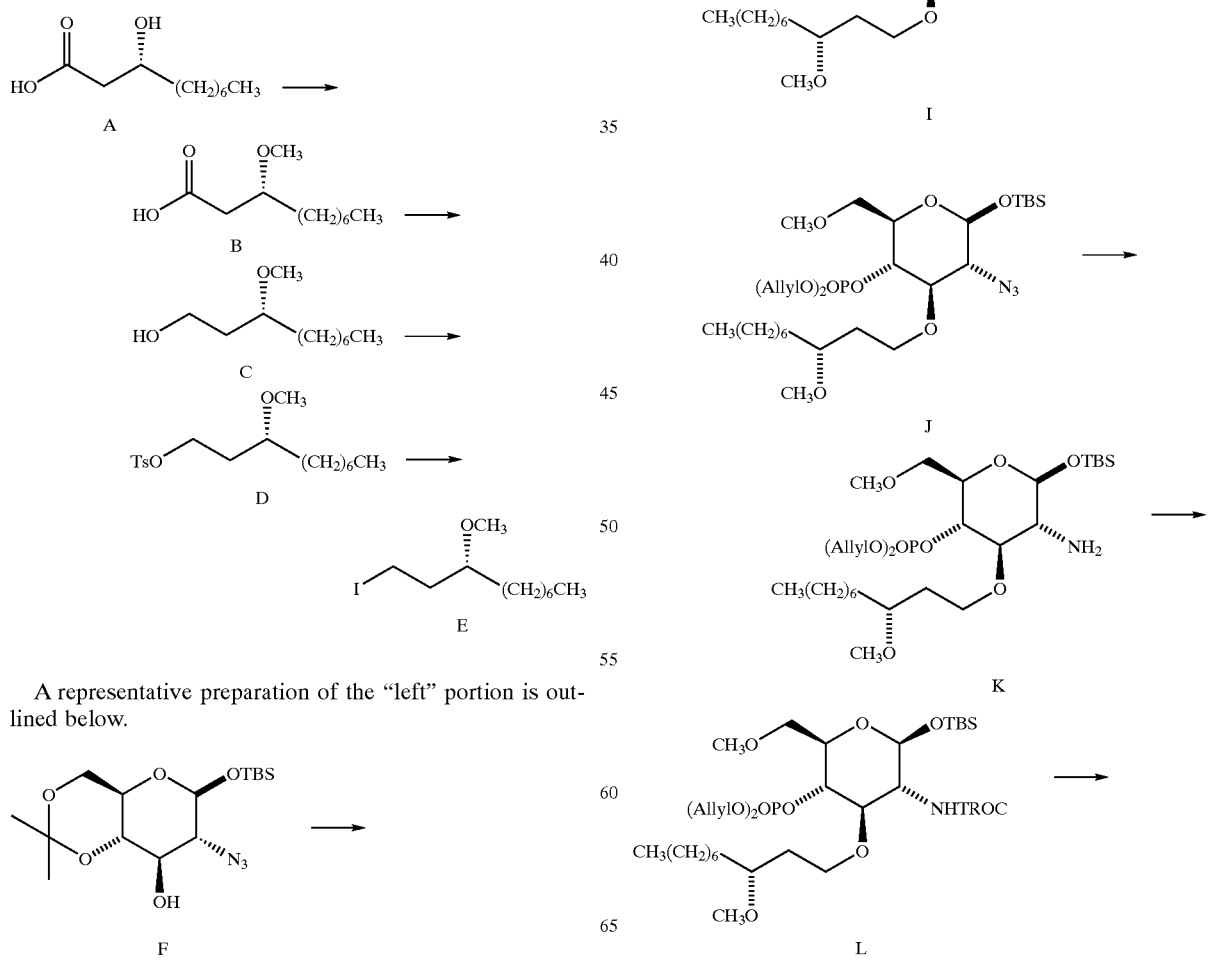

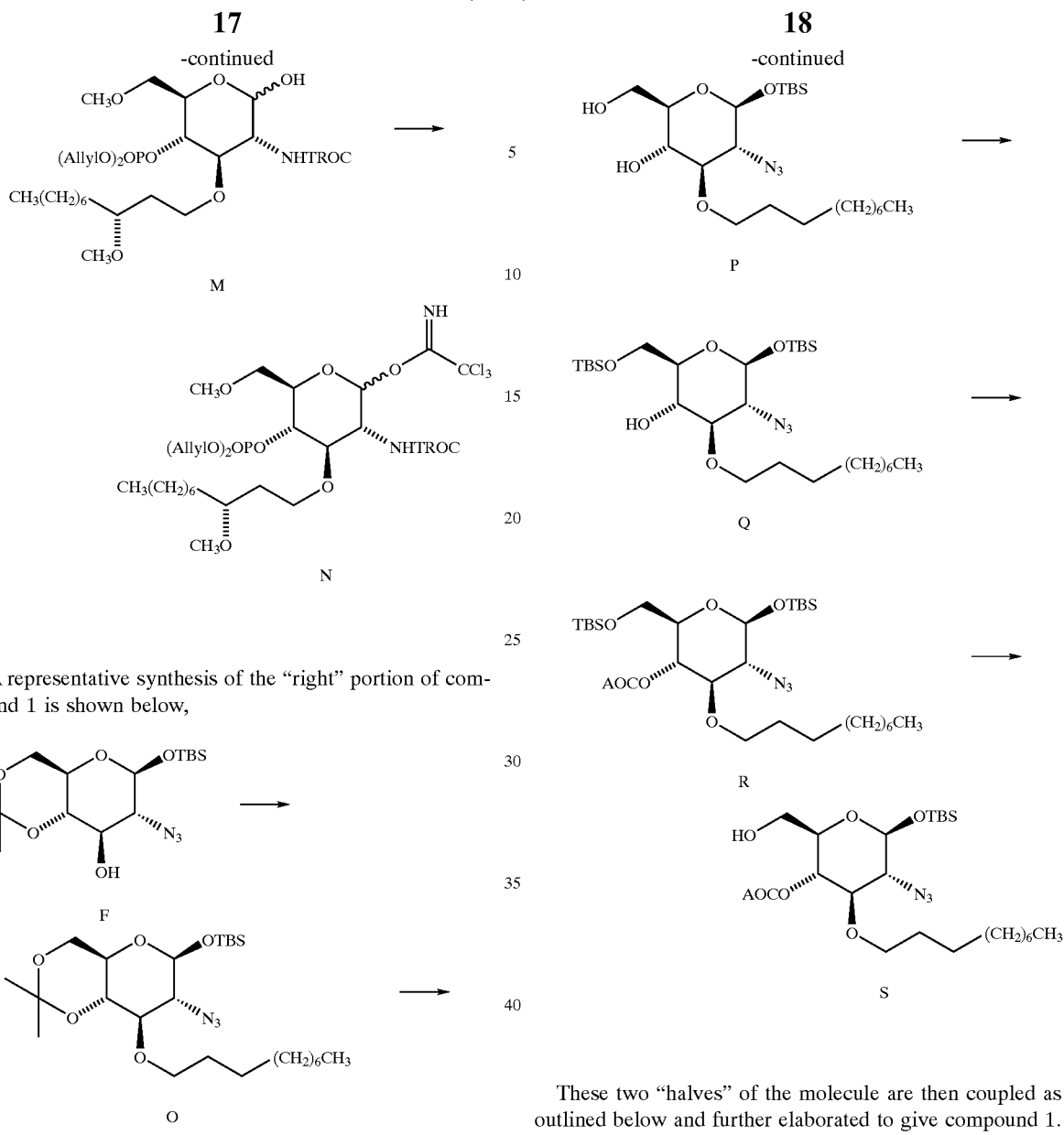
A representative synthesis of the "right" portion of compound 1 is shown below,
These two "halves" of the molecule are then coupled as outlined below and further elaborated to give compound 1.
Compound 1 (sodium salt)
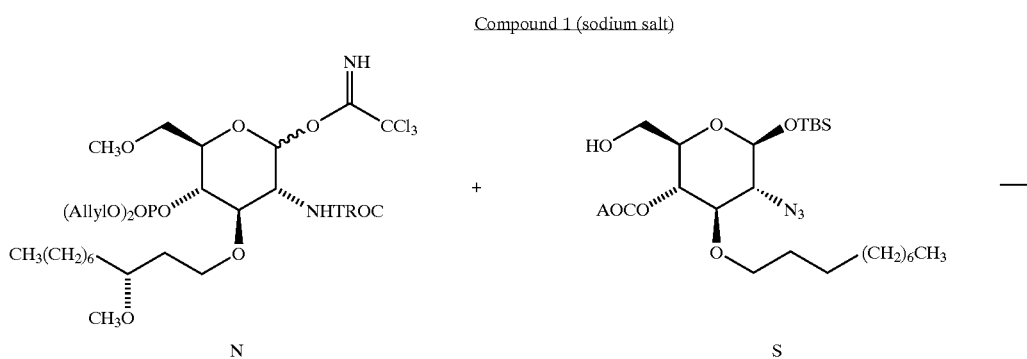

-continued
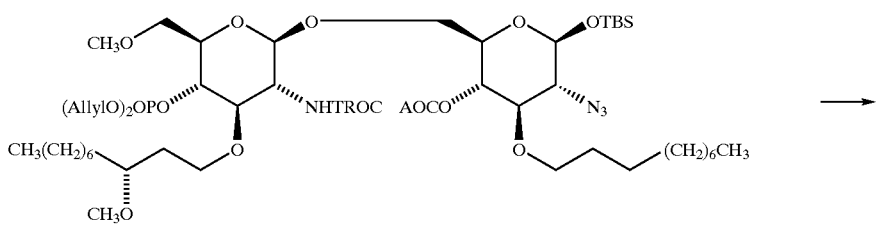
T
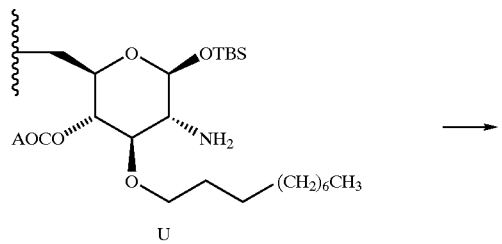
U
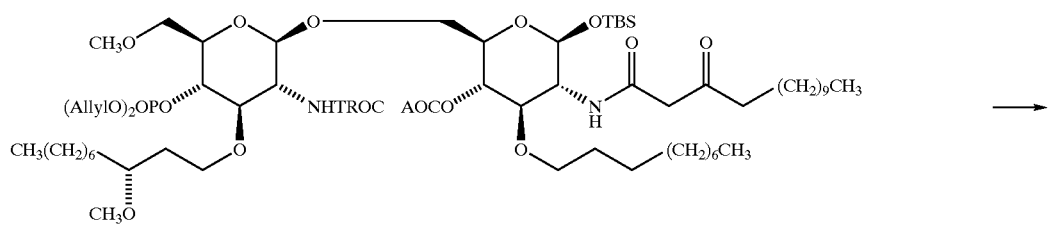
V
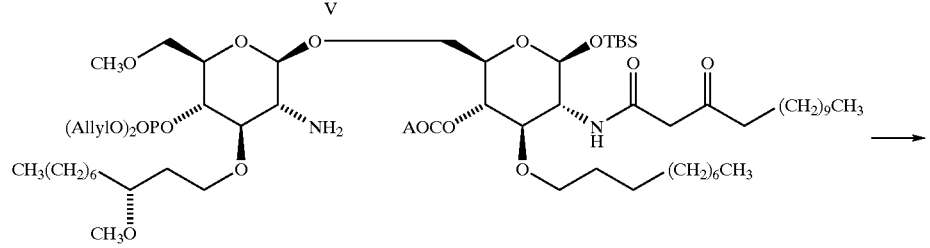
W
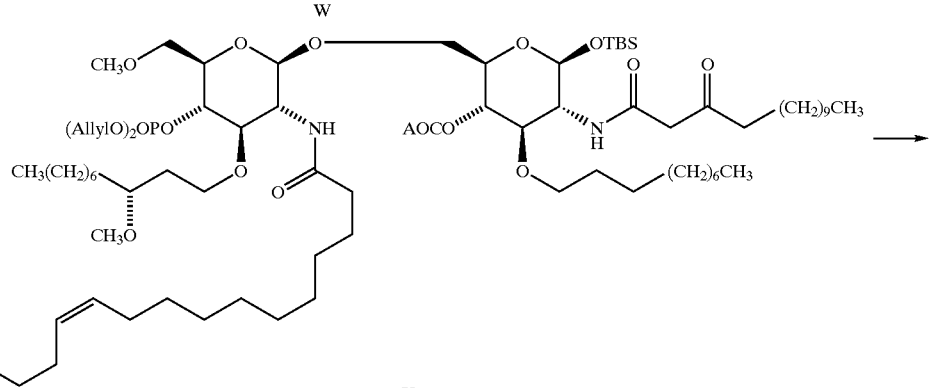
X
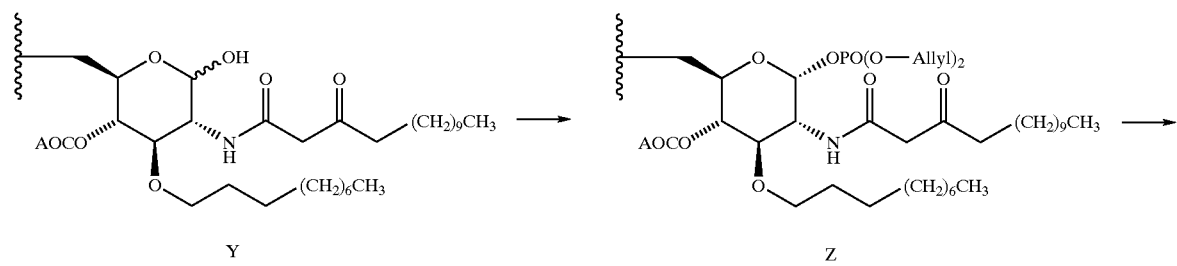
Y                                                                    Z -continued

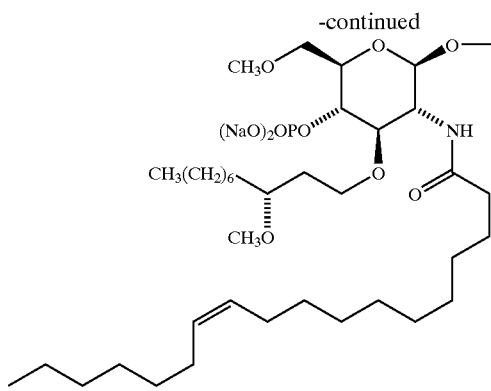
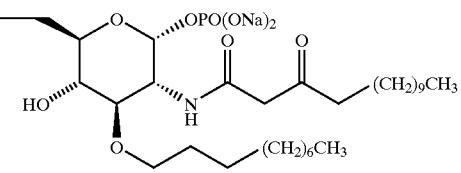

Formulations

The lipid A analogs described herein are administered to the respiratory tract of a human subject who has, or is at risk of having, pulmonary bacterial infection or symptomatic pulmonary exposure to endotoxin. Depending on the circumstances, administration can be chronic or acute. In the case of chronic administration, therapy is maintained over a prolonged period of time (in some cases, for the duration of a person's lifetime), so that the concentration of drug in the airway surface fluid or serum is maintained at a therapeutically or prophylactically effective level throughout the course of treatment. Acute drug administration is carried out in circumstances in which a short-term pulmonary exposure to bacteria and/or endotoxin has been diagnosed, including a recently diagnosed bacterial infection or the risk of an imminent infection.

Chronic Treatment

Chronic administration of the lipid A analog can be effected by means of periodic bolus administration, by continuous, metered inhalation, or by a combination of the two. A single dose is administered by inhalation 1 $\mu$g–24 mg, for example, 5–150 $\mu$g, or, preferably, 10–100 $\mu$g of the drug. Of course, recalcitrant disease may require administration of relatively high doses, e.g., 5 mg, the appropriate amounts of which can be determined by one of skill in this art. Appropriate frequency of administration can be determined by one of skill in this art, and can be, for example, 1–4, for example, 2–3, times each day. Preferably, the drug is administered once each day.

One of the primary categories of conditions requiring chronic administration is inborn or acquired predisposition to pulmonary bacterial infection. Examples of conditions in this category are:

Cystic fibrosis
Immune deficiencies, including:
  Immunocompromise due to anti-cancer therapy
  Immunocompromise due to anti-rejection therapy after organ transplant
  Asplenia
  Hypogammaglobulinemia
  Dysglobulinemias
  Deficiencies of complement cascade components
  HIV infection, or other viral infections
  Polymorphonuclear granulocyte defects
Ciliary dyskinesias (e.g., Kartagener's syndrome)
Obstructive pulmonary disorders, including:
  Congestive heart failure with pulmonary edema
  Chronic obstructive pulmonary disease
  Tumors leading to bronchial obstruction
  Bronchiectasis (e.g., as a complication of asthma)

Acute Treatment

Acute administration of the lipid A analog, like chronic administration, can be effected by bolus or continuous administration, or by a combination of the two. The difference is in the duration of treatment: while chronic treatment can be carried out for weeks, months, or even years, acute treatment typically is carried out for periods of hours or days. A single dose is administered by inhalation of 1 $\mu$g–24 mg, for example, 5–150 $\mu$g, or, preferably, 10–100 $\mu$g of the drug. Of course, recalcitrant disease may require administration of relatively high doses, e.g., 5 mg, the appropriate amounts of which can be determined by one of skill in this art. Appropriate frequency of administration can be determined by one of skill in this art, and can be, for example, 1–4, for example, 2–3, times each day. Preferably, the drug is administered once each day.

The dosage of drug delivered acutely over a 24 hour period can be higher than the chronically delivered dose. However, generally, if discrete bolus administration is employed, administration is carried out one to six times over a 24 hour period. Administration of the drug can take place until the symptoms of pulmonary bacterial infection or pulmonary exposure to endotoxin in the patient have lessened to a satisfactory extent, or, preferably, have disappeared. It may be necessary, in some cases, to continue administration for several days, e.g., one, two, three, or four weeks.

Acute administration generally is carried out either prophylactically or immediately following either diagnosis of an endotoxin exposure or the existence of a condition that would predispose a patient to a pulmonary bacterial infection. One set of such predisposing conditions is occupations that predictably involve inhalation of particulate matter. The drug can be routinely administered to workers in such occupations before exposure to the particulate matter. These conditions include:

Exposure to plant (e.g., grain or cotton) product dusts
Exposure to bacteria-laden aerosols (e.g., from sewage, contaminated water, garbage, or human waste)
Exposure to inhalable mineral particulates that damage the integrity of the lung (e.g., silica)

Another category of conditions requiring acute drug administration is acute lung injuries that predispose to infection, increase sensitivity to endotoxin, or affect ability to clear endotoxin. These include:

Smoke inhalation or heat exposure (e.g., thermal injury; inhalation of hot air or steam)

Aspiration of gastric contents

Near-drowning

Inhalation of noxious substances

Examples of a final category of conditions or circumstances that can predispose to pulmonary bacterial infection or increase sensitivity to endotoxin are listed below; for the most part, these require acute drug administration, but, in some cases, where the condition persists long-term, chronic administration is required:

Trauma (e.g., chest trauma)

Mechanical ventilation

Intubation with an endotracheal tube

Cigarette smoking (emphysema; tendency towards bronchitis)

Intravenous substance abuse

Chronic exposure to polluted air

Seizure disorders (increased risk of aspiration, leading to, e.g., chemical injury by stomach acid)

Alcoholism (increased risk of aspiration, leading to, e.g., chemical injury by stomach acid)

Intestinal ischemia and reperfusion

Renal failure/uremia

Hypotension and shock

Hepatic disease, including cirrhosis

Pancreatitis

Malnutrition

Thermal injuries

Viral pneumonias, including those caused by Myxovirus (e.g., influenza)

Intravascular infections (e.g., infective endocarditis)

Both chronic and acute administration can employ standard pulmonary drug administration formulations. Administration by this route offers several advantages, for example, rapid onset of action by administering the drug to the desired site of action, at higher local concentrations. Pulmonary drug formulations are generally categorized as nebulized and aerosolized formulations, which are each described further, as follows.

Nebulizers employ drug in droplet form, in solution or suspension, with a pharmaceutically acceptable liquid carrier. Examples of this approach, such as jet nebulization, are described, e.g., in Flament et al., Drug Development and Industrial Pharmacy 21(20):2263–2285, 1995. Briefly, in such methods, air is passed rapidly through a narrow orifice of a tube by the use of a pump, the pressure of the air falls, creating a vacuum, which results in suction of liquid contained in a reservoir connected with the tube. The suctioned liquid is thus reduced to a fine spray or mist that can be inhaled.

Aerosols are dry powder formulations that usually are delivered via pressurized, metered dose inhalers (pMDIs). Aerosol formulation techniques, which can be applied for use in the present invention, are described, e.g., by Sciarra, "Aerosols," Chapter 92 in *Remington's Pharmaceutical Sciences*, 16$^{th}$ edition (ed. A. Osol), pp. 1614–1628. Use of pMDIs has some drawbacks, such as employing chlorofluorocarbon propellants, which are damaging to the environment. Thus, alternatives, such as dry powder inhalers, spacer devices, and holding chambers, can be used (see, e.g., Malcolmson et al., PSTT 1(9):394–398, 1998, and Newman et al., "Development of New Inhalers for Aerosol Therapy," in Proceedings of the Second International Conference on the Pharmaceutical Aerosol, pp. 1–20).

It will be understood, however, that the specific dose level for any particular patient will depend on a variety of factors, including the activity of the specific compound employed; the age, body weight, general health, and sex of the individual being treated; the time and route of administration; the rate of excretion; other drugs that have previously been administered; and the severity of the particular disease undergoing therapy.

EXAMPLES

Examples of use of the method of the invention include the following. The compounds of this invention and their preparation can be understood further by the examples, which illustrate some of the processes by which these compounds are prepared or used. These examples should not be construed as specifically limiting the invention and variations of the invention, now known or later developed, are considered to fall within the scope of the present invention as hereinafter claimed.

Compounds of the present invention are referred to by compound number according to the tables below.

Formula 1

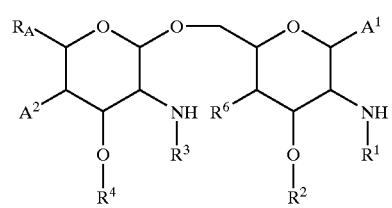

| Compound # | $A^1/A^2$ | $R^1$ | $R^2$ | $R^3$ | $R^4$ | $R_A$ | $R^6$ |
|---|---|---|---|---|---|---|---|
| 1 | $OPO(OH)_2$ | $COCH_2CO(CH_2)_{10}CH_3$ | $(CH_2)_9CH_3$ | $CO(CH_2)_9CH=CH(CH_2)_5CH_3$ | $(CH_2)_2CH(OCH_3)(CH_2)_6CH_3$ | $CH_2OCH_3$ | $OH$ |
| 2 | $OPO(OH)_2$ | $COCH_2CO(CH_2)_{10}CH_3$ | $(CH_2)_9CH_3$ | $CO(CH_2)_9CH=CH(CH_2)_5CH_3$ | $(CH_2)_2CH(OH)(CH_2)_6CH_3$ | $CH_2OCH_3$ | $OH$ |
| 3 | $OPO(OH)_2$ | $COCH_2CO(CH_2)_{10}CH_3$ | $(CH_2)_9CH_3$ | $CO(CH_2)_{16}CH_3$ | $(CH_2)_2CH(OH)(CH_2)_6CH_3$ | $CH_2OCH_3$ | $OH$ |
| 4 | $OPO(OH)_2$ | $COCH_2CHOH(CH_2)_{10}CH_3$ | $(CH_2)_9CH_3$ | $CO(CH_2)_9CH=CH(CH_2)_5CH_3$ | $(CH_2)_2CH(OH)(CH_2)_6CH_3$ | $CH_2OCH_3$ | $OH$ |
| 5 | $OPO(OH)_2$ | $COCH_2CO(CH_2)_{10}CH_3$ | $(CH_2)_9CH_3$ | $CO(CH_2)_9CH=CH(CH_2)_5CH_3$ | $(CH_2)_9CH_3$ | $CH_2OCH_3$ | $OH$ |
| 6 | $OPO(OH)_2$ | $CO(CH_2)_9CH=CH(CH_2)_5CH_3$ | $(CH_2)_9CH_3$ | $CO(CH_2)_9CH=CH(CH_2)_5CH_3$ | $(CH_2)_2CH(OH)(CH_2)_6CH_3$ | $CH_2OCH_3$ | $OH$ |
| 7 | $OPO(OH)_2$ | $CO(CH_2)_{12}CH_3$ | $(CH_2)_9CH_3$ | $CO(CH_2)_9CH=CH(CH_2)_5CH_3$ | $(CH_2)_2CH(OH)(CH_2)_6CH_3$ | $CH_2OCH_3$ | $OH$ |

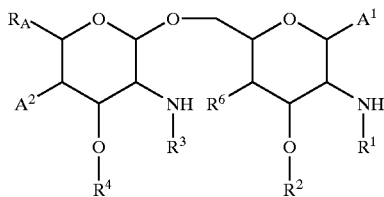

Formula 1

| Compound # | $A^1/A^2$ | $R^1$ | $R^2$ | $R^3$ | $R^4$ | $R_A$ | $R^6$ |
|---|---|---|---|---|---|---|---|
| 8 | $OPO(OH)_2$ | $COCH_2CH(OCH_3)(CH_2)_{10}CH_3$ | $(CH_2)_9CH_3$ | $CO(CH_2)_9CH=CH(CH_2)_5CH_3$ | $(CH_2)_2CH(OCH_3)(CH_2)_6CH_3$ | $CH_2OCH_3$ | OH |
| 9 | $OPO(OH)_2$ | $COCH_2CH(OCH_3)(CH_2)_{10}CH_3$ | $(CH_2)_9CH_3$ | $CO(CH_2)_9CH=CH(CH_2)_5CH_3$ | $(CH_2)_2CH(OH)(CH_2)_6CH_3$ | $CH_2OCH_3$ | OH |
| 10 | $OPO(OH)_2$ | $COCH_2CH(OH)(CH_2)_{10}CH_3$ | $(CH_2)_9CH_3$ | $CO(CH_2)_9CH=CH(CH_2)_5CH_3$ | $(CH_2)_2CH(OCH_3)(CH_2)_6CH_3$ | $CH_2OCH_3$ | OH |
| 11 | $OPO(OH)_2$ | $COCH_2CO(CH_2)_{10}CH_3$ | $(CH_2)_9CH_3$ | $CO(CH_2)_9CH=CH(CH_2)_5CH_3$ | $(CH_2)_2CH(OCH_3)(CH_2)_6CH_3$ | $CH_3$ | OH |

Chemical Examples

Unless otherwise noted, all reactions were conducted under an inert atmosphere. Intermediates and final products gave spectral analysis (for example, nuclear magnetic resonance spectroscopy and/or mass spectroscopy) consistent with their proposed structures. Reactions were monitored by silica gel thin layer chromatography. Preparative chromatography, unless otherwise noted, was performed on silica gel.

Preparation of Compound 1 (1287: SGEA) by Route 1

All sensitive reactions were run under nitrogen and in dry equipment, and anhydrous sodium sulfate used as the drying agent, unless otherwise specified. All products gave satisfactory nuclear magnetic resonance spectra.

Purification of

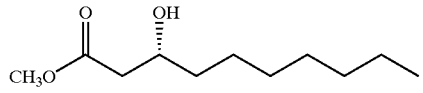

The material (5 kg) was chromatographed on silica and eluted with a gradient of hexane and EtOAc (100% to 33% hexane). The pure fractions were combined and distilled (97–100° C. at 0.15 mm Hg). Yield of purified material 4,513 g.

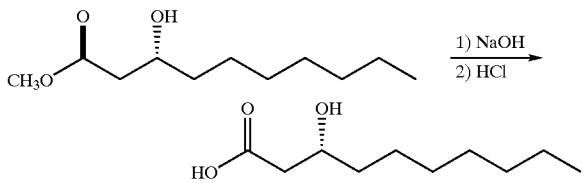

To an ice-cold solution of the ester (4500 g, 22.2 moles) in 12.6 L of THF was added sodium hydroxide (27 moles) in 10.8 L of water. The mixture was stirred briefly and 2.5 L of concentrated hydrochloric acid was added. The layers were separated and the aqueous layer re-extracted with EtOAc. The combined organic layers were washed with brine, dried over sodium sulfate, and concentrated. The product slowly crystallized to give 2983 g of white powder.

Purification of

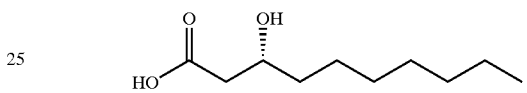

To a solution of the acid (15.8 moles) in 33 L of acetonitrile was added dicyclohexylamine (16.7 moles). The solution was heated to 60° C. and allowed to cool overnight. The crystals were collected, washed twice with solvent, and recrystallized from acetonitrile. To a suspension of previously methanol-washed Amberlite IR-120 Plus (12 kg) in EtOAc (24 L) and water (24 L) was added the above-described salt. The mixture was stirred for several hours and the organic layer was separated. The aqueous layer was re-extracted with EtOAc (12 L) and the combined organic layers were dried (sodium sulfate) and concentrated to give 2,997 g of a white solid.

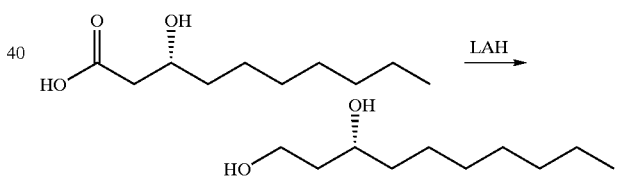

To a hot (~67° C.) 1 M solution of lithium aluminum hydride (8 L) in THF was slowly added a solution of the acid (1 kg) in 4 L of THF. The solution was allowed to cool overnight. The solution was slowly added to 1 M aqueous HCl (5 L). The mixture was extracted with toluene (12 L). The organic layer was washed with sodium bicarbonate solution, dried (sodium sulfate), and the solvent removed under vacuum to give a syrup, which was distilled (103° C.) to give 914 g of a light yellow oil.

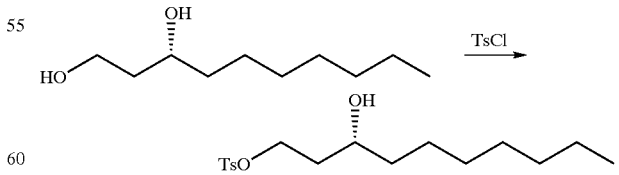

To a 0° C. solution of the diol (913.8 g) in pyridine (3 L) was added 3 L of triethylamine, followed by a solution of tosyl chloride (1 kg) in pyridine (1.5 L) and triethylamine (1.5 L). The mixture was allowed to warm overnight and poured onto a cold solution of 6 M aqueous HCl (16 L) and methylene chloride (8 L). The organic layer was separated and the aqueous layer extracted with additional methylene chloride. The combined organic layers were dried (sodium sulfate) and the solvent removed under reduced pressure. The residue was chromatographed twice on silica and eluted with a gradient of hexane:EtOAc (9:1 to 1:6) to give 642 g of tosylate.

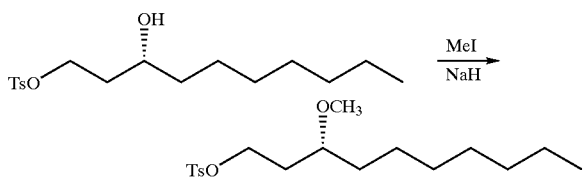

To a suspension of 60% sodium hydride oil dispersion (8.68 moles) in 1.15 L of DMF and 1.1 L of THF was slowly added the tosylate (1.139 kg) and methyl iodide (7.7 kg) in 1.15 L of DMF and 1.1 L of THF. The mixture was stirred overnight, then diluted with DMF (3 L), and slowly added to a saturated aqueous solution of ammonium chloride. The mixture was extracted with hexane (8 L), which was dried (sodium sulfate) and the solvent removed to give a orange/brown oil. The oil was chromatographed on silica and eluted with a gradient (hexane:EtOAc 100:0 to 6:1) to give 940 g of a light yellow oil.

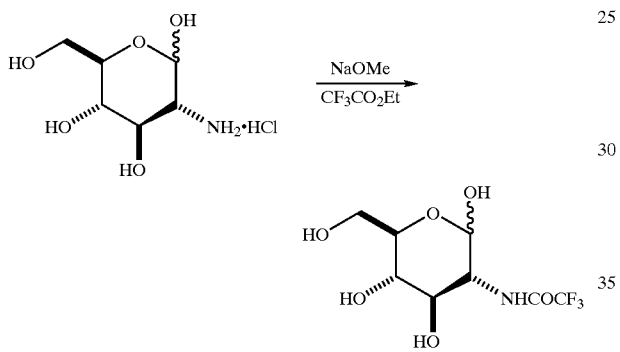

To a suspension of the aminosugar (1019 g) in 5 L of MeOH was added a 25% solution of NaOMe in MeOH (1080 mL, 5 moles), followed by 610 mL of ethyl trifluoroacetate. The mixture was stirred overnight, the solvent removed under reduced pressure, and the residue titurated with isopropanol. The mixture was filtered and the residue washed with additional isopropanol, to give 1369 g of product.

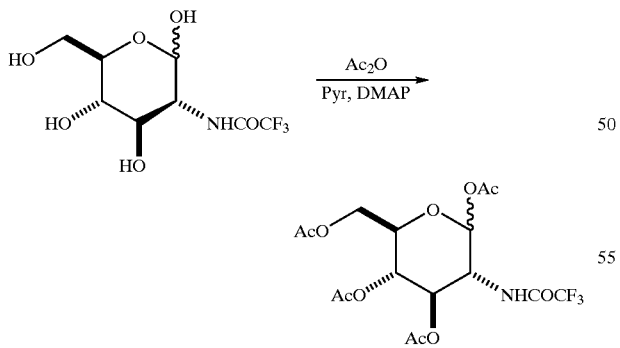

To a suspension of the hydroxy sugar (1300 g) in pyridine (4 L) was added dimethylaminopyridine (79 g), followed by acetic anhydride (2713 mL). The mixture was stirred overnight. The solvent was removed under reduced pressure. Toluene (5×500 mL) was added and also removed under reduced pressure, to give a solid, which was chromatographed on silica. Elution with hexane:EtOAc (1:1) gave 1479 g of a white solid.

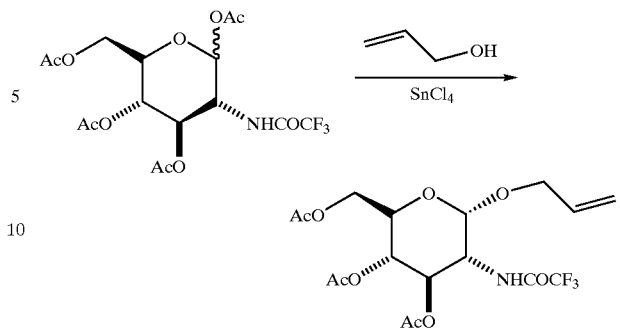

To a solution of the acetylated sugar (1479 g) in 8 L of methylene chloride was added allyl alcohol (764 mL), followed by slow addition of tin tetrachloride (976 mL). The mixture was stirred overnight and slowly poured onto ice-cold water (7.5 L). The organic layer was separated and the aqueous layer washed with additional methylene chloride. The combined organic layers were washed with aqueous sodium bicarbonate, dried, and concentrated under reduced pressure. The residue was chromatographed on silica (7.5 kg) and eluted with a hexane:EtOAc gradient (4:1 to 1:1) to give 1327 g of a pale yellow oil.

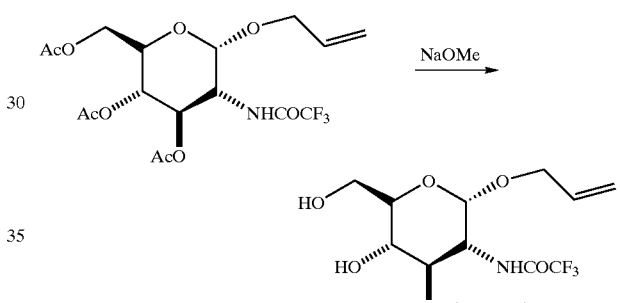

To an ice-cold solution of protected sugar (1322 g) in 8.5 L of methanol was added a 25% solution of NaOMe in methanol (437 mL) over one hour. To this was added previously washed 1740 g of Amberlite IR-120 Plus resin. The mixture was filtered, concentrated, and the residue chromatographed on silica. Elution with methanol gave 907 g of product.

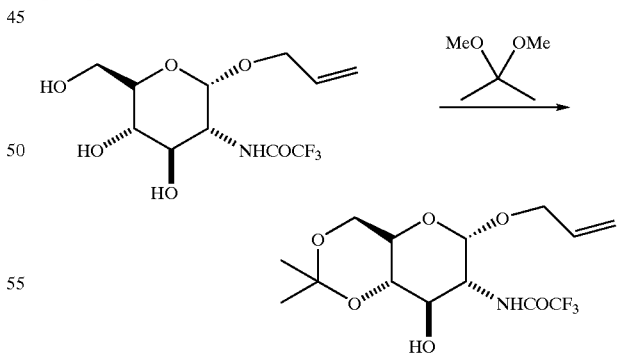

The triol was suspended in acetone (7.5 L) and camphorsulfonic acid (85 g) was added, and then 2,2-dimethoxypropane (965 mL) was slowly added. The mixture was stirred overnight, followed by the addition of triethylamine (51 mL). The solvent was removed under reduced pressure to give a brown solid, which was chromatographed on silica. Elution with a hexane:EtOAc gradient (3:1 to 2:1) gave 842 g of a semi-white gum.

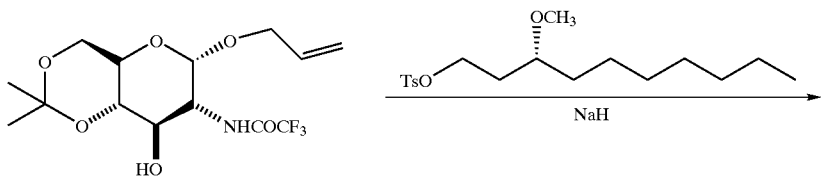

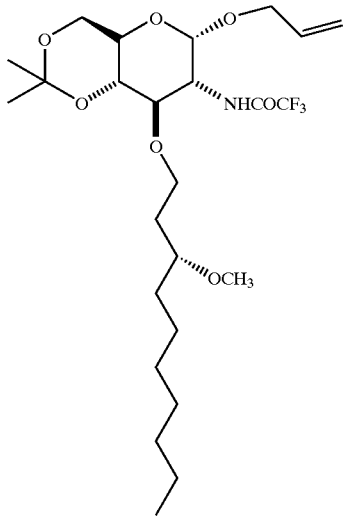

To a suspension of 60% sodium hydride oil dispersion (82 g) in 2.2 L of THF and 580 mL of DMF and was added the tosylate (351 g) and a solution of the free alcohol (400 g) in a mixture of 1360 mL of THF and 360 mL of DMF. The mixture was stirred overnight. The mixture was cooled in ice and methanol was added, followed by water (2 L). The mixture was extracted three times with EtOAc. The combined organic layers were dried and concentrated. The resulting mixture was chromatographed on silica. Gradient elution with hexane:EtOAc (19:1 to 1:1) gave 711 g.

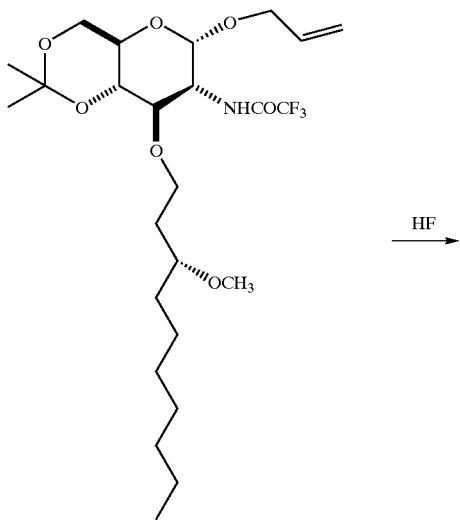

-continued

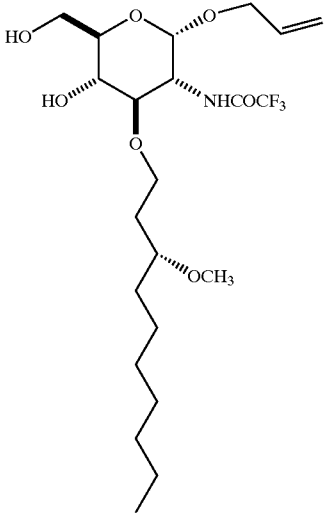

To a mixture of 48% aqueous hydrofluoric acid in 1500 mL of acetonitrile in a Teflon bottle was added a solution of the starting material (613 g) in 750 mL of acetonitrile and 750 mL of methylene chloride. The mixture was stirred for one hour and poured onto 8 L of water. The mixture was extracted with methylene chloride (4×2 L). The combined organic layers were washed with aqueous saturated sodium bicarbonate solution, dried, and concentrated under reduced pressure. The residue was chromatographed on silica. Gradient elution with methylene chloride:methanol (39:1 to 9:1) gave 519 g of product.

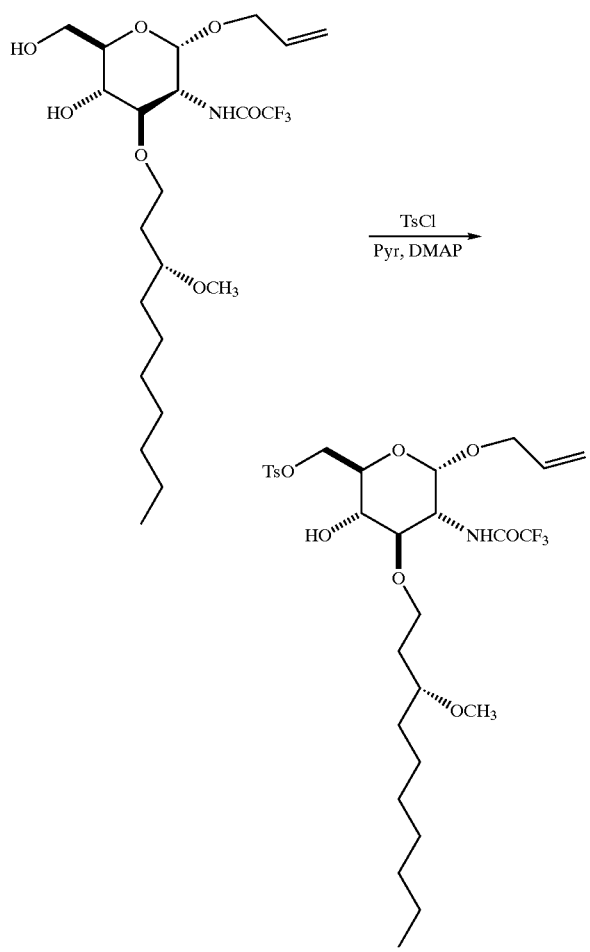

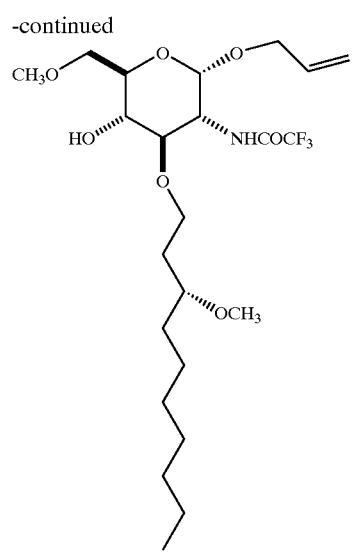

To a solution of the diol (577 g) in pyridine (5 L) was added tosyl chloride (339 g) and N,N-dimethylaminopyridine (14.5 g). The mixture was stirred at RT for two days and then poured onto 14 L of cold aqueous 1 M hydrochloric acid. The mixture was extracted (2×5 L) with methylene chloride. The combined organic layers were dried and concentrated. The residue was chromatographed on silica. Gradient elution (hexane:EtOAc, 6:1 to 1:1) gave 632 g of a yellow syrup, which slowly crystallized on standing.

To an 85° C. solution of 25% sodium methoxide in methanol (1825 mL) in DMF (1365 mL) was added the tosylate (714 g) in DMF (1365 mL) over 1.25 hour. The mixture was stirred 30 minutes and cooled to 4° C. and poured onto an ice-cold mixture of aqueous 1 M hydrochloric acid and 4.6 kg of ice. The mixture was stirred for 30 minutes and filtered. The filtrate was washed with 2 L of water and the combined aqueous layers were extracted with 2×4 L of EtOAc. The combined organic layers were dried and concentrated. The residue was purified by chromatography on silica. Gradient elution (hexane:ethyl acetate 3:1 to 1:1) gave 549 g of a pale yellow to white solid.

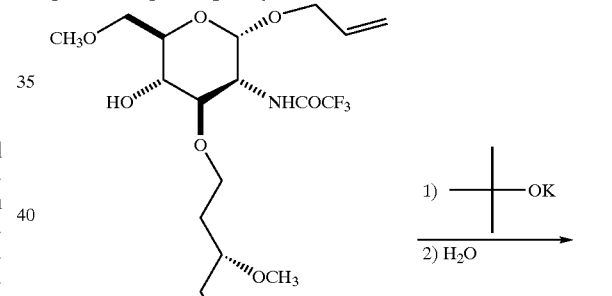

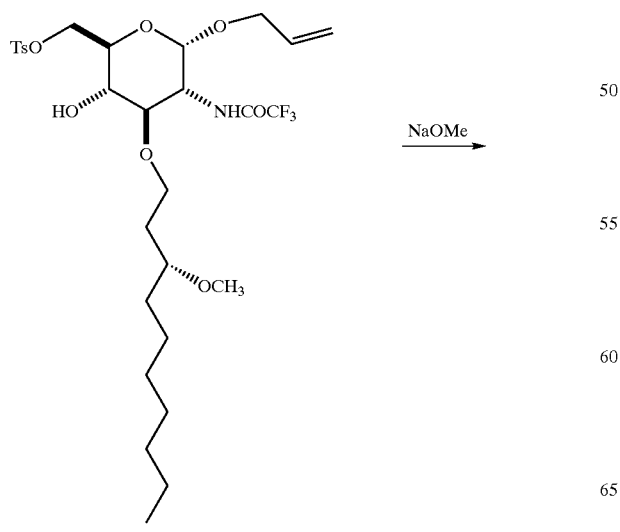

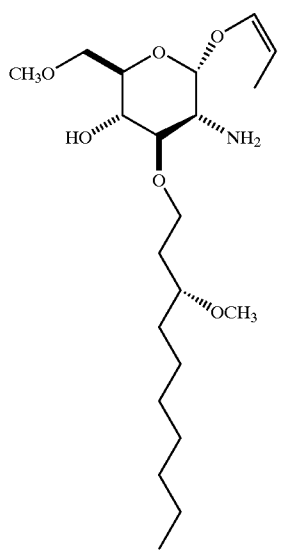

This reaction was run under argon. To a solution of potassium t-butoxide (139 g) in 440 mL of DMSO was added a solution of the sugar (247 g) in 440 mL of anhydrous DMSO. The mixture was heated to 85° C. for 1.5 hour and then 250 mL of water was added and the mixture heated overnight at 85° C. and cooled in an ice bath. The mixture was poured onto 3.5 L of brine and the mixture extracted with 3×750 mL of methylene chloride. The combined organic layers were dried and concentrated to yield 560 g of a brown oil.

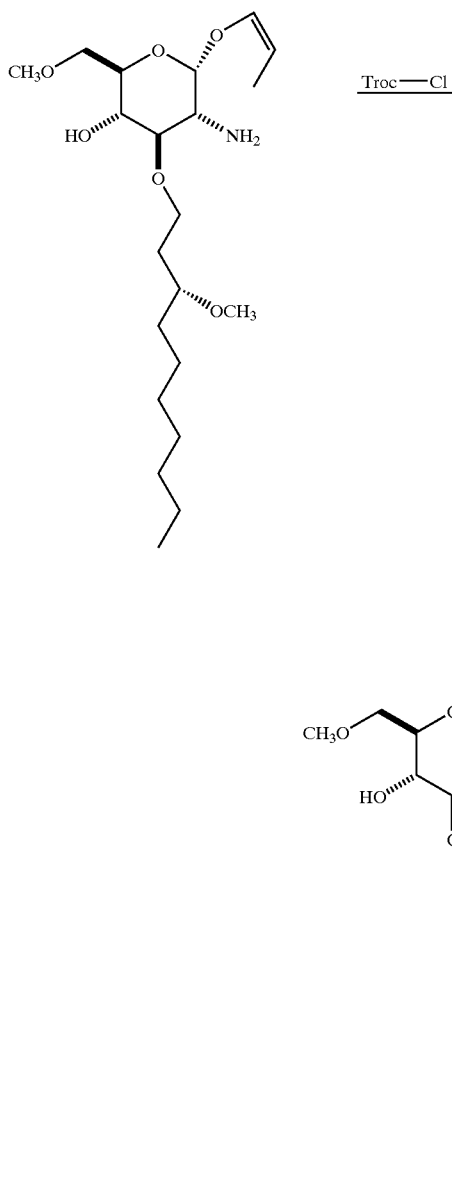

To a mixture of the free amine (199 g) 780 mL of THF and 390 mL of saturated aqueous sodium bicarbonate was added Troc-Cl (157 g). After ½ hour, the mixture was slowly poured onto a solution of 500 mL of 40% aqueous methylamine and 3 L of water. The mixture was extracted with 2×1750 mL of methylene chloride. The combined organic layers were dried and concentrated. The residue was chromatographed on silica. Gradient elution with hexane: EtOAc (5:1 to 1:1) gave a quantitative yield of 287 g of a yellow to off-white solid.

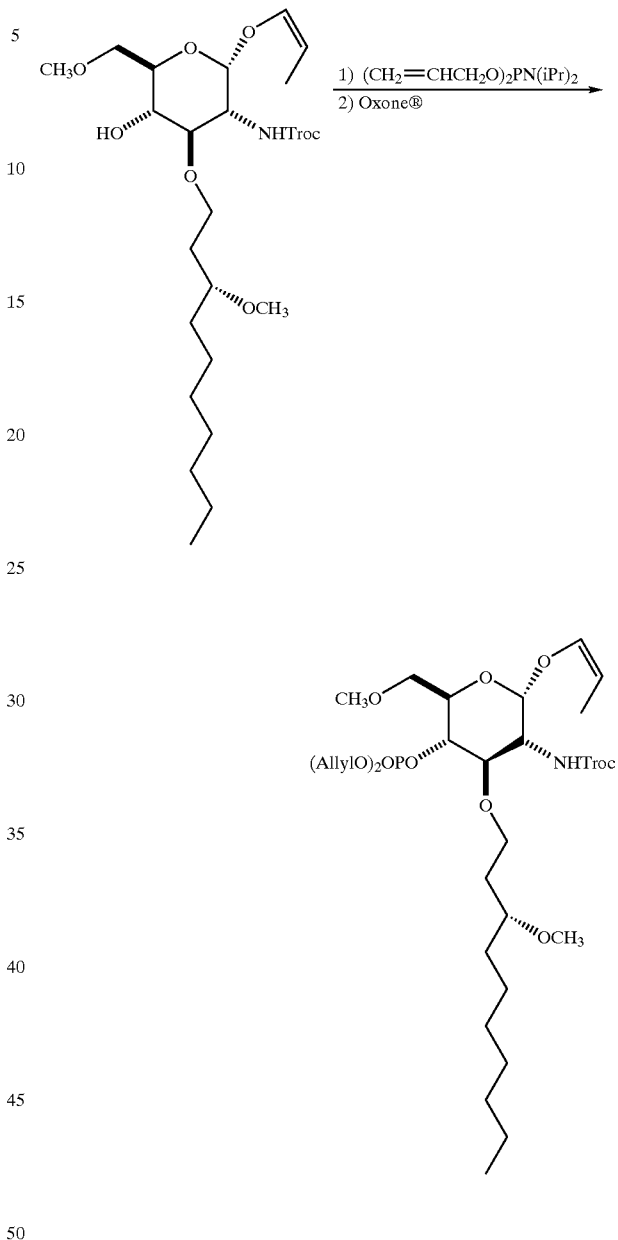

To a solution of the hydroxy-sugar in 2 L of methylene chloride was added tetrazole (155.6 g), followed by diallyl-diisopropylphosphoramidite (182 mL). After ½ hour, the mixture was poured onto an ice-cold mixture of Oxone® (potassium peroxymonosulfate) (455.6 g), water (1.25 L) and THF (2.5 L). After 15 minutes, this mixture was poured onto cold 10% aqueous sodium thiosulfate. After 15 minutes, the mixture was extracted with 2 L of methylene chloride. The organic layer was separated, the aqueous layer re-extracted with methylene chloride and the combined organic layers dried and the solvent removed under vacuum. The residue was chromatographed on silica. Gradient elution with hexane/ethyl acetate (6:1 to 2:1) gave 205.7 g of pale yellow syrup.

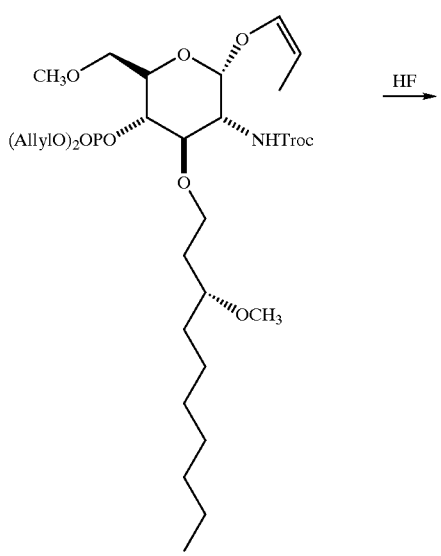

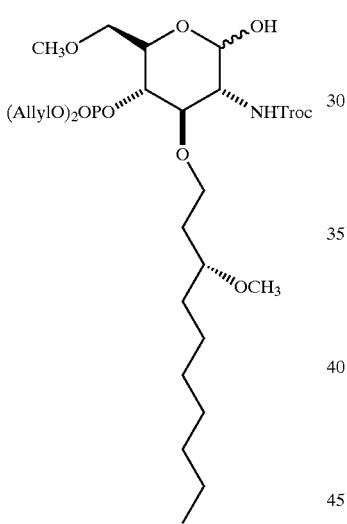

To a solution of 48% aqueous hydrofluoric acid, 400 mL, in acetonitrile, 1.2 L in a Teflon container was added a solution of the sugar, 138.8 g, in methylene chloride, 500 mL. The mixture was stirred overnight, diluted with water, 3 L, and extracted with methylene chloride, 2.4 L. The organic layer was washed with aqueous sodium bicarbonate solution, dried and the solvent was removed under reduced pressure. The residue was chromatographed on silica. Gradient elution (hexane:ethyl acetate 2:1 to 1:1), followed by elution with a gradient of methylene chloride: methanol (19:1 to 9:1) gave 129.2 g as a waxy gum.

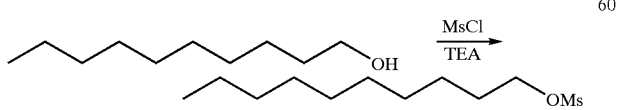

To an ice-cold solution of 450 g of 1-decanol in 685 mL of triethylamine and 1125 mL of methylene chloride was added 330 mL of mesyl chloride. The cooling bath was removed after 1½ hour and the solvent removed under reduced pressure. To the residue was added 2.5 L of 1 M aqueous hydrochloric acid. This mixture was extracted 3×2 L of methylene chloride. The organic layers were combined, dried and the solvent removed under reduced pressure. The residue was chromatographed on silica. Elution with 1:1 hexane:ethyl acetate gave 651 g of product.

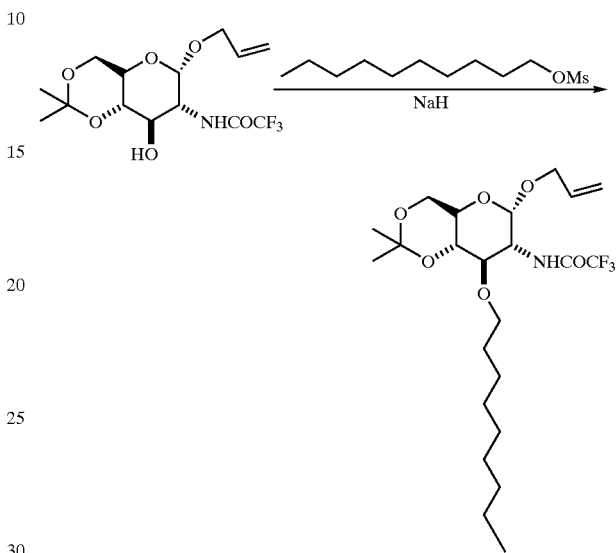

To a suspension of 60% sodium hydride mineral oil dispersion in 1 L of THF and 470 mL of DMF was added a solution of the alcohol in 280 mL of DMF and 1 L of THF over 1 hour. The mesylate, 470 g, was then added over 15 minutes. After 2 days, 400 mL of methanol was added, followed by 4 kg of ice and 4 L of water. This mixture was extracted with 2×4 L of ethyl acetate. The combined organic layers were dried and the solvent was removed under reduced pressure. The residue was chromatographed on silica. Gradient elution with hexane:EtOAc (39:1 to 2:1) gave 618 g.

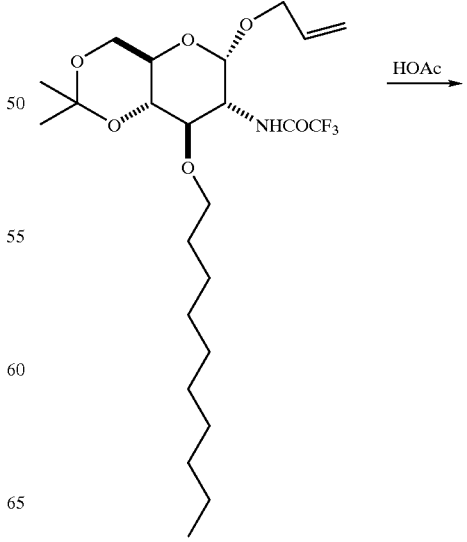

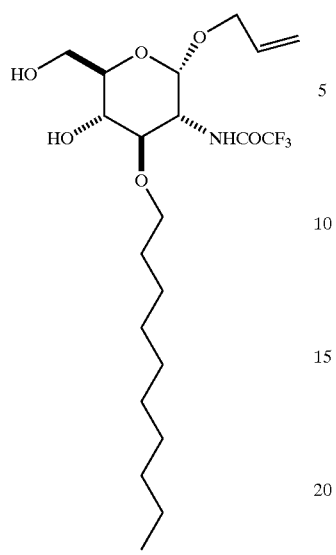

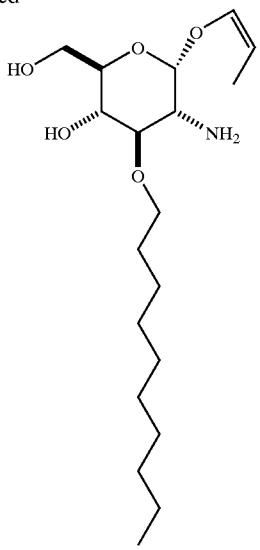

A solution of the sugar, 520 g, in 5.2 L of glacial acetic acid and 1.3 L of water was stirred overnight. It was poured onto 7.5 L of water and filtered. The filtrate was dried by azeotropic distillation with toluene (3×500 mL) under reduced pressure to give 458 g.

This reaction was run under argon. To a suspension of potassium t-butoxide, 295 g, in DMSO, 1 L, was added a solution of 340 g of the sugar in 1.5 L of DMSO. The mixture was heated to 85° C. for 1¼ hour and 1.4 L of 3 M aqueous potassium hydroxide was added and the mixture stirred overnight at 85° C. The mixture was cooled to room temperature and poured onto a mixture of 3.5 L of brine and 3.5 L of water. The mixture was extracted three times with methylene chloride, the mixture dried and the solvent was removed under reduced pressure. The residue was chromatographed on silica. Gradient elution with methylene chloride:methanol (19:1 to 4:1) gave 740 g of product.

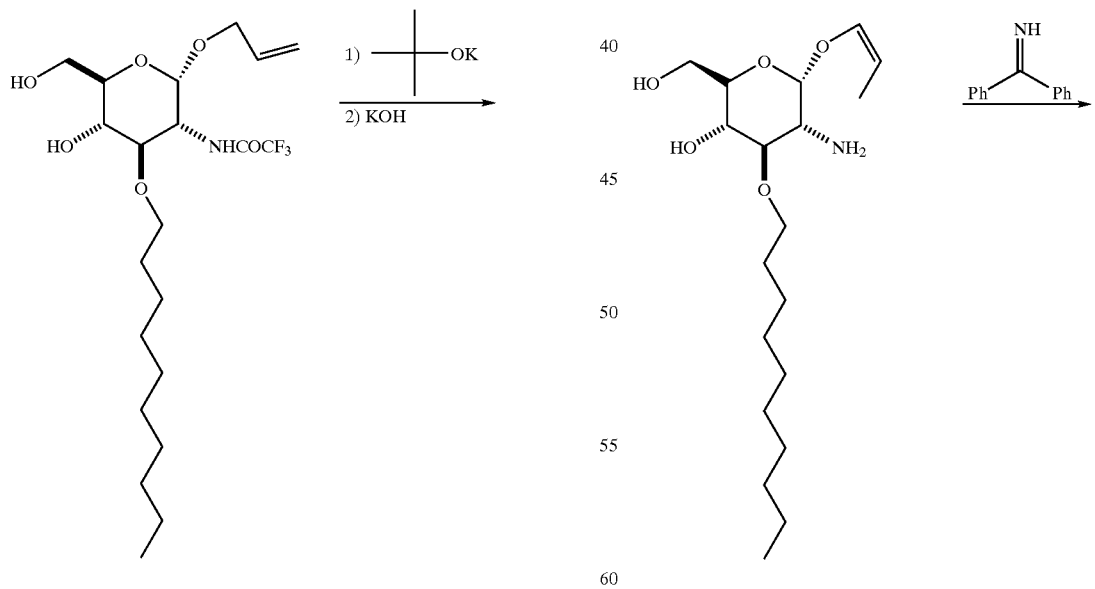

-continued

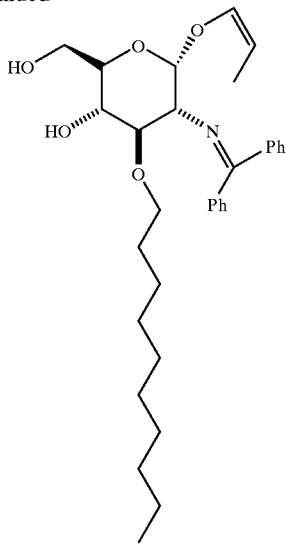

A solution of the aminosugar, 740 g, in benzophenone imine, 338 g, was heated at 45° C. overnight. The mixture was chromatographed on silica and eluted with a gradient of hexane/ethyl acetate (39:1 to 1/1) to give 371 g of a pale yellow solid.

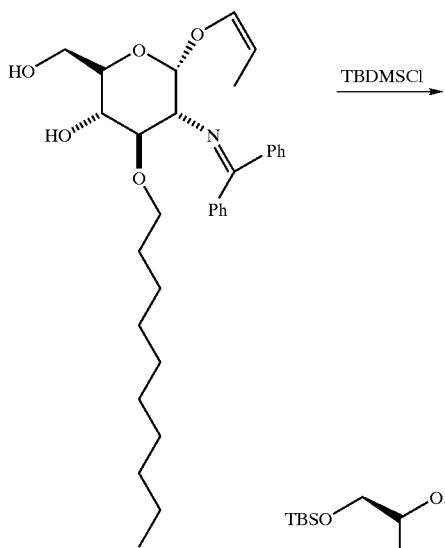

TBDMSCl →

To a solution of the diol sugar, 366 g, in 1.3 L of DMF was added imidazole, 118 g, followed by t-butyldimethylsilyl chloride, 117 g. After 5 minutes, the mixture was poured onto 1.4 L of aqueous saturated sodium bicarbonate. The mixture was extracted with ethyl acetate three times. The organic layers were combined, the solvent was removed under reduced pressure and the residue chromatographed on silica. Gradient elution with hexane/ethyl acetate (49:1 to 4:1) gave 446 g of a syrup.

1) COCl₂
2) allyl alcohol

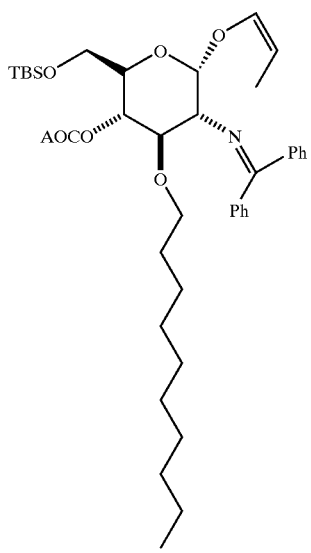

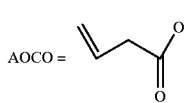

AOCO = was added and the solution stirred for 10 minutes. Allyl alcohol, 469 mL, was added. After 40 minutes, saturated aqueous sodium bicarbonate solution, 2.3 L, was added and the mixture extracted with ethyl acetate. The organic layer was separated, dried, and the solvent was removed under reduced pressure. The residue was chromatographed on silica. Gradient elution with hexane/ethyl acetate (49:1 to 4:1) gave 441 g of yellow syrup.

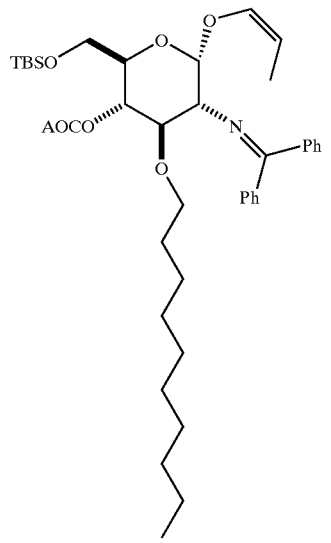

HOAc/H₂O →

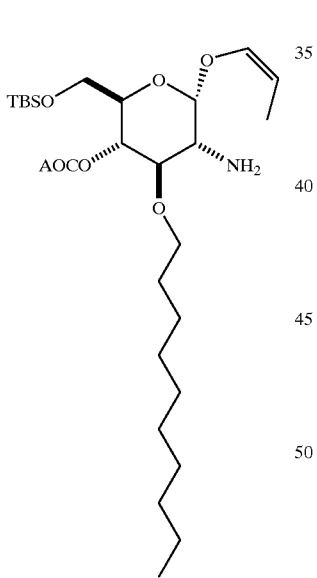

To a solution of the sugar, 431 g, in THF, 200 mL, was added glacial acetic acid, 330 mL, and water, 110 mL. The mixture was stirred for three hours, cooled in ice, and 6.6 L of 1 M aqueous sodium hydroxide was added. The mixture was extracted with methylene chloride, 2×2 L. The combined organic layers were dried and the solvent was removed under reduced pressure. The residue was chromatographed on silica. Gradient elution with methylene chloride:methanol (19:1 to 4:1) gave the amine, 309 g, as a syrup.

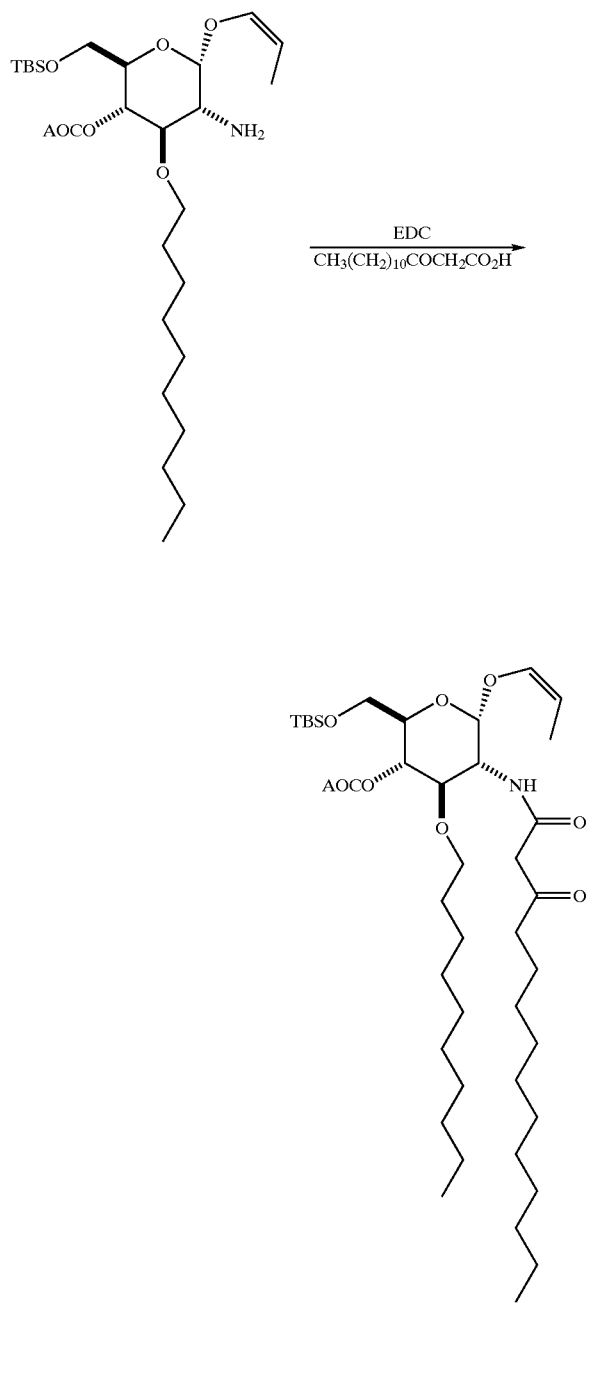

To an ice-cold solution of the amino sugar, 309 g, in 3 L of methylene chloride was added 1-(3-dimethylaminopropyl)-3-ethylcarbodiimide hydrochloride (EDC), 435 g, followed in 10 minutes by the carboxylic acid, 275 g. After 10 minutes, the mixture was extracted with saturated aqueous sodium bicarbonate. The organic layer was separated, the aqueous layer re-extracted with methylene chloride, the combined organic layers dried, and the solvent was removed under reduced pressure. The residue was chromatographed on silica. Gradient elution (hexane:ethyl acetate 19:1 to 3:1) gave 338 g of pale yellow syrup.

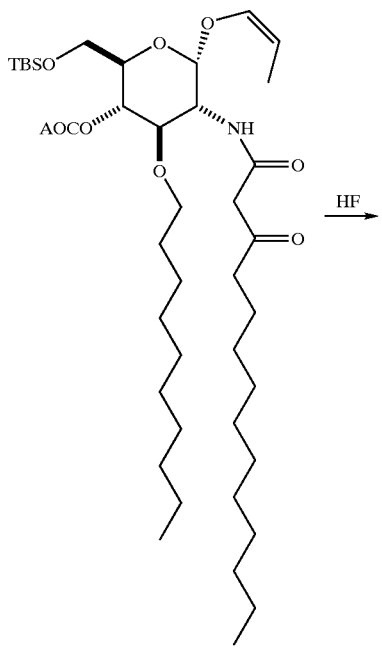

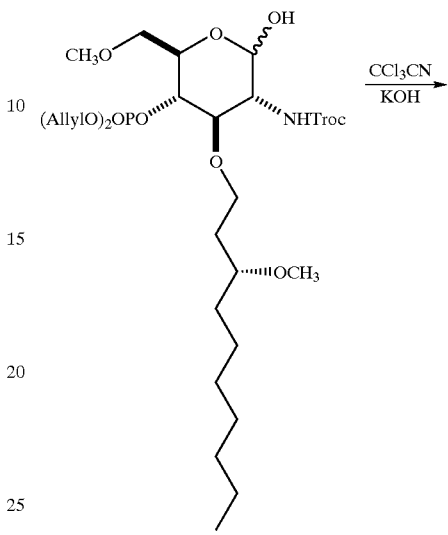

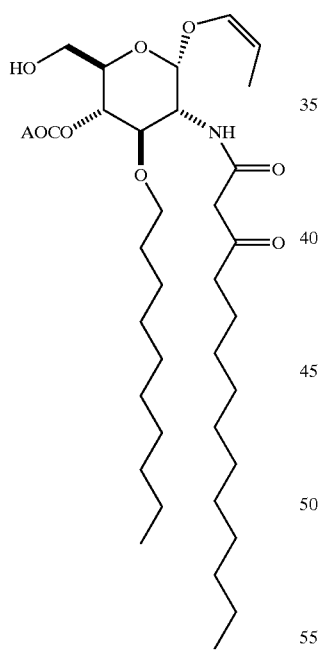

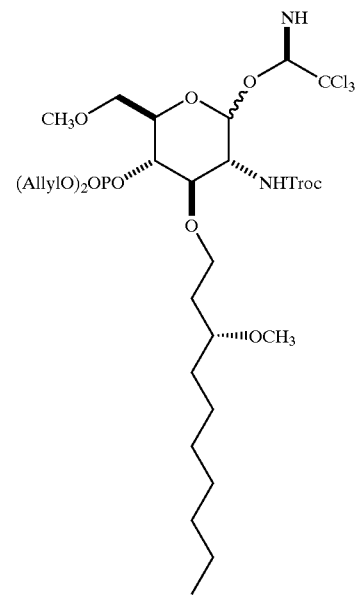

To a solution of 48% aqueous hydrofluoric acid, 11 mL, in acetonitrile 293 mL, was added 4.6 g of silica gel, followed by a solution of the sugar, 146.7 g, in methylene chloride, 147 mL. After one half-hour, the mixture was diluted with water, 975 mL, and extracted with methylene chloride. The organic layer was separated and the aqueous layer re-extracted with methylene chloride. The combined organic layers were washed with aqueous sodium bicarbonate solution, dried, and the solvent was removed under reduced pressure. The residue was chromatographed on silica. Gradient elution (hexane:ethyl acetate 5:1 to 0:1) gave 110.4 g of an off-white waxy solid.

To a solution of the sugar, 129 g, in 500 g of trichloroacetonitrile was added potassium carbonate, 240 g. The mixture was stirred for one half-hour and filtered through diatomaceous earth. The filter cake was washed with methylene chloride and the filtrates combined and the solvent was removed under reduced pressure. The residue was chromatographed on silica. Gradient elution (hexane:ethyl acetate 1:1 to 0:1) gave 145.7 g of a yellow gum.

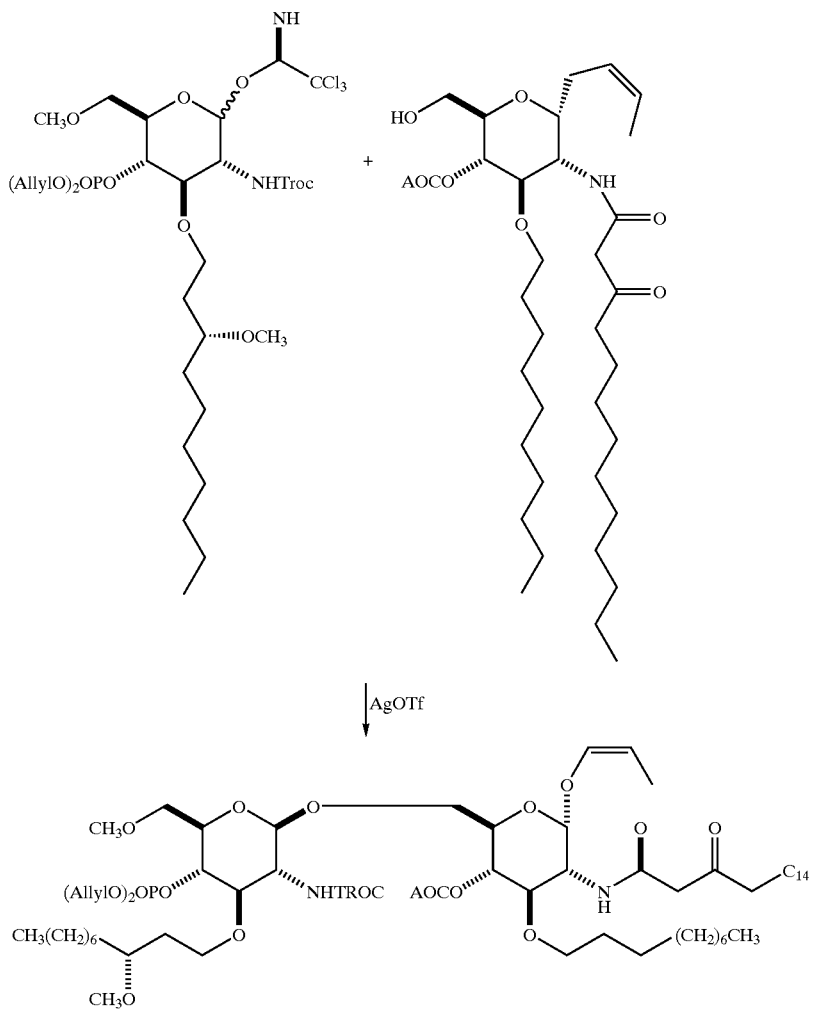

The left sugar, 145.7 g, and of the right sugar, 109.2 g, were azetropically dried by evaporating toluene (3×200 mL). A solution of the two sugars in 750 mL of methylene chloride was added to an ice-cold solution of silver triflate, 62.7 g, in 130 mL of methylene chloride. The mixture was warmed to room temperature and stirred overnight. The mixture was poured onto a mixture of saturated aqueous sodium bicarbonate and sodium thiosulfate solution. The organic layer was separated and the aqueous layer washed with methylene chloride. The combined organic layers were dried and the solvent was removed under reduced pressure. The residue was chromatographed twice on silica. Gradient elution with hexane:ethyl acetate (5:1 to 1:1) gave 189.56 g of a sticky foam.

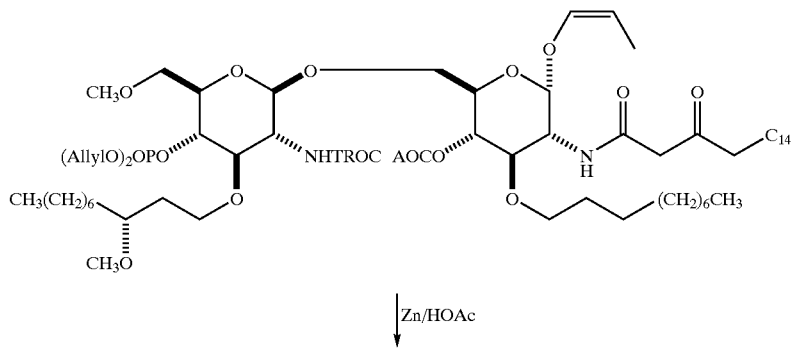

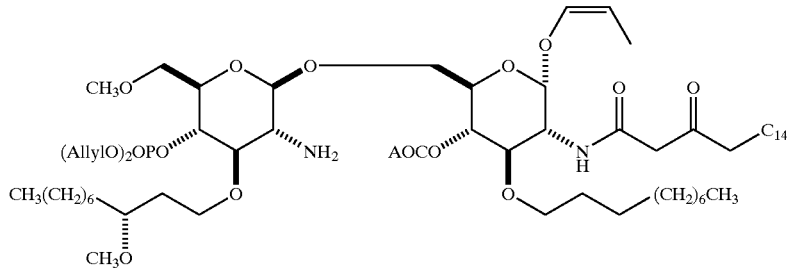

To a solution of the disaccharide, 188.7 g, in THF, 590 mL, was added zinc dust, 457.6 g, followed by glacial acetic acid, 395 mL. After one half-hour, the mixture was filtered through diatomaceous earth and the filter cake washed with THF. The organic layers were combined and the solvent was removed under reduced pressure. The residue was dried azeotropically by distilled benzene from the residue (4×250 mL) to give 223.1 g of a pink gum.

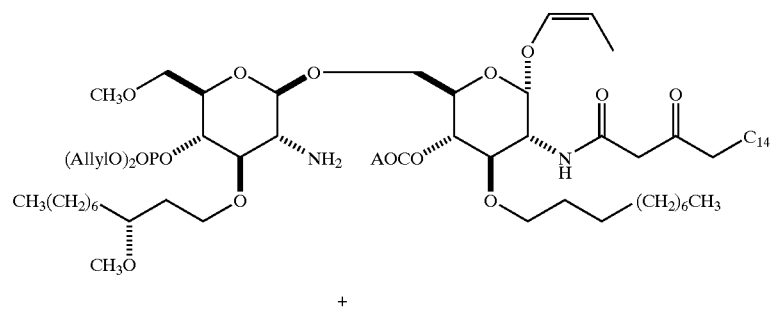

+

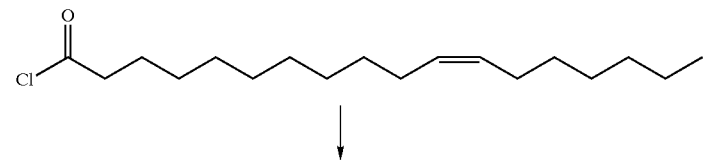

↓

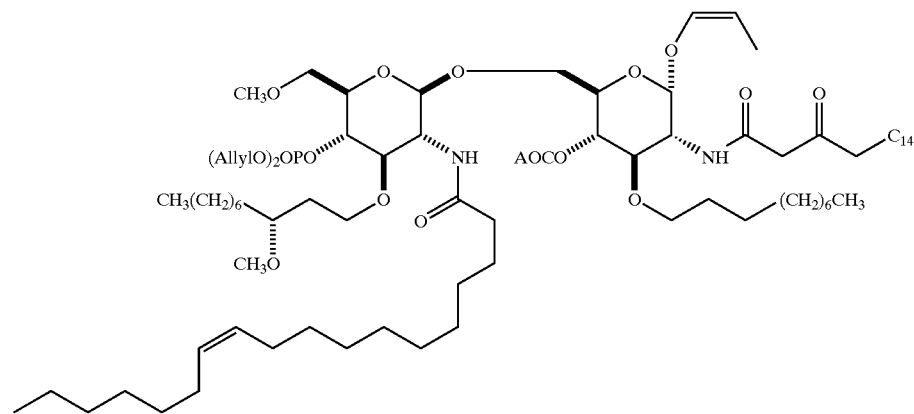

To a solution of the sugar, 223.1 g, in 1.3 L of THF was added a solution of sodium bicarbonate, 37.5 g, in 250 mL of water. Cis-11-Octadecenoyl chloride, 67.4 g, was added. After 10 minutes, the mixture was extracted twice with ethyl acetate. The combined organic layers were dried and the solvent was removed under reduced pressure. The residue was chromatographed on silica. Gradient elution with hexane:ethyl acetate (2:1 to 0:1) gave 160.2 g of pale yellow wax.

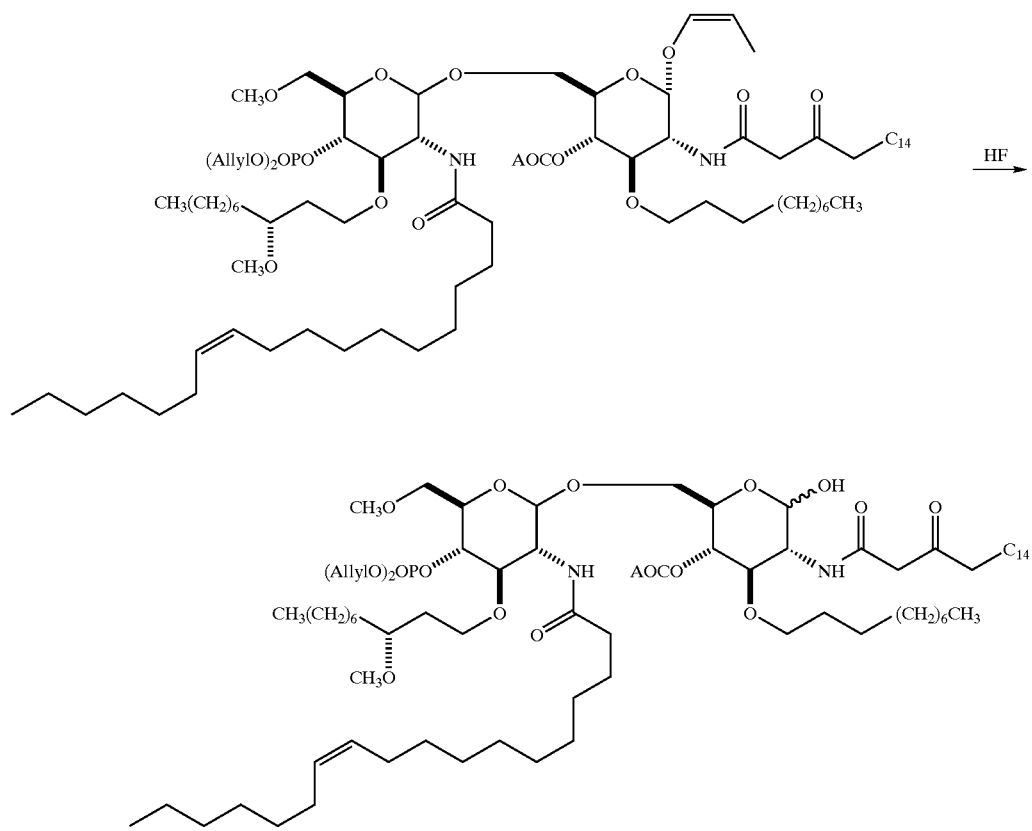

A solution of the sugar, 161.3 g, in methylene chloride, 215 mL, in a Teflon bottle was added to a solution of 48% hydrofluoric acid, 150 mL, in acetonitrile, 474 mL. After four hours, the mixture was poured onto 500 mL of water. The mixture was extracted twice with methylene chloride. The combined organic layers were washed with aqueous saturated sodium bicarbonate, dried, and the solvent was removed under reduced pressure. The residue was chromatographed on silica. Gradient elution (methylene chloride: ethyl acetate:methanol 500:500:20 to 500:500:160) gave a yellow waxy gum.

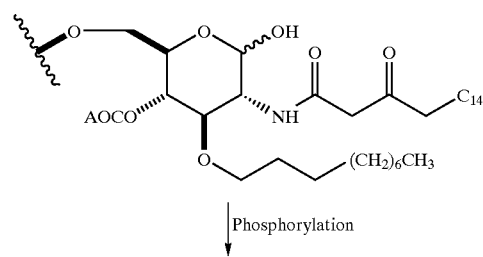

-continued

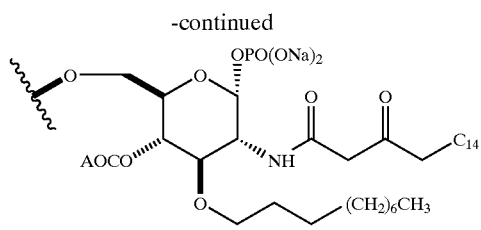

The sugar, 719 mg, was dissolved in methylene chloride and sodium sulfate (1.4 g) was added. Diallyldiiospropylphosphoramidite (189 μL) and tetrazole (162 mg) were added, the mixture stirred for 10 minutes, and then cooled to −78° C. A solution of m-chloroperoxybenzoic acid (192 mg) in methylene chloride (4 mL) was added dropwise. The mixture was washed with aqueous sodium thiosulfate and with aqueous sodium bicarbonate, dried (sodium sulfate), and the solvent removed under reduced pressure. The residue was chromatographed to give 660 mg.

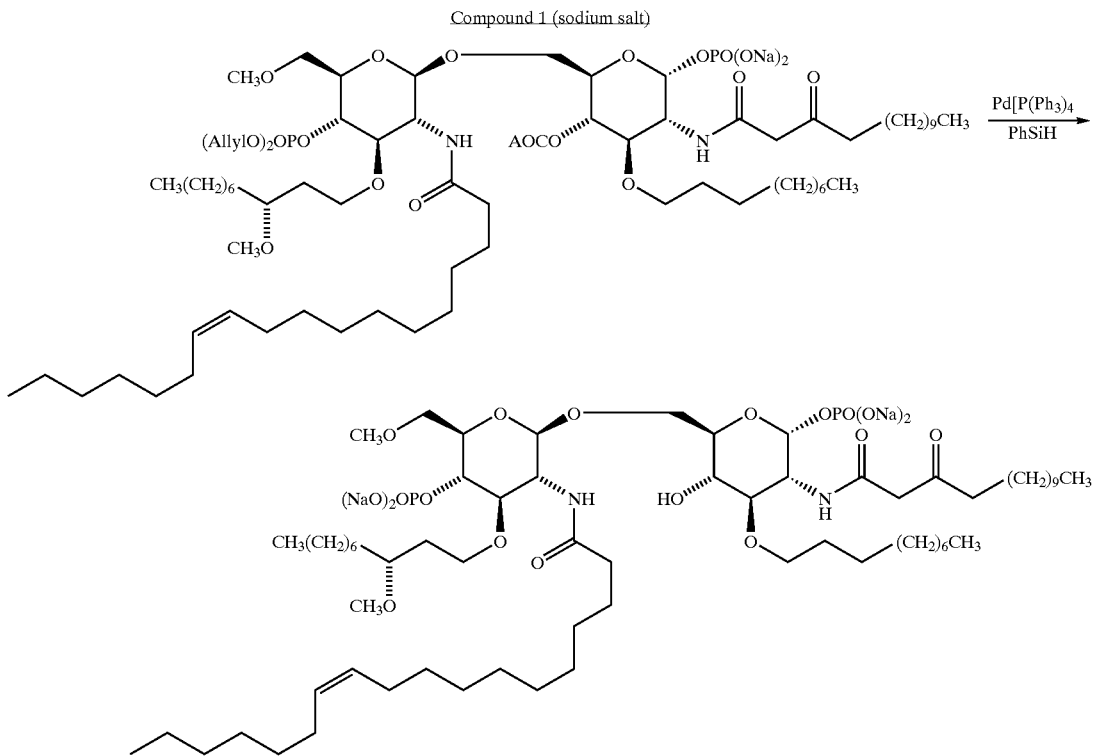

To a solution of tetrakis(triphenylphosphine)palladium (0) (166 mg) in 2 mL of tetrahydrofuran:acetic acid (10:1) mixture was added a solution of intermediate Z (660 mg) in 3 mL of the same solvent mixture. After 30 minutes, additional tetrakis(triphenylphosphine)palladium (0) was added. After an additional 1½ hours, toluene was added, and the solvent removed under reduced pressure. The mixture was purified by chromatography on diethylaminoethylcellulose. The purified mixture was dissolved in 0.1 N aqueous sodium hydroxide, filtered through a 0.45 μm sterile filter, and purified by HPLC on a YMC-Pack ODS-AP column to give 130 mg of compound 1.

Analytical data for compound 1 made by the methods described above is given below:

Compound 1: $^1$H NMR (CD$_3$OD) δ: 5.3 (1H, m), 4.6 (1, m), 4.0 (m, m), 3.9 (1H, d), 3.7 (1H, t), 3.6 (1H, t), 3.4 (3H, s), 3.3 (3H, t), 2.6 (2H, t), 2.3 (2H, m), 2.0 (2H, m), 1.7–1.2 (m, m), 0.9 (6H, t).

$^{31}$P NMR (CD$_3$OD) δ: 4.71, 3.98.

Preparation of Compound 1 by Route 2

Preparation of Compound 1

Example 1

Intermediate B

To a suspension of intermediate A (15 g), prepared by the method of Christ et al., European patent application 92309057.5, in CH$_2$Cl$_2$ (150 mL) and 48% HBF$_4$ (29.2 g), cooled via ice-bath, was added TMSCHN$_2$ (165 mL as a 2M solution in hexane). The mixture was stirred until the reaction was almost complete by TLC and then methanol (20 mL) was added followed by acetic acid (10 mL). Aqueous sodium bicarbonate was added and the mixture extracted with methylene chloride. The mixture was dried (sodium sulfate) and the solvent removed under reduced pressure. Chromatography of the residue gave B, 14.9 g.

Example 2

Intermediate C

To a cold (0° C.) solution of B (14.9 g) in methylene chloride (100 mL) was slowly added diisobutylaluminum hydride (140 mL as a 1M solution in hexanes) until reaction was complete, as determined by TLC. The reaction was quenched by the addition of aqueous 1N hydrochloric acid (100 mL) followed by concentrated hydrochloric acid (50 mL). The layers were allowed to separate, and the aqueous layer was re-extracted with CH$_2$Cl$_2$. The combined organic layers were then washed with brine, dried over sodium sulfate, and concentrated under reduced pressure. After purification by silica chromatography, 12.06 g of intermediate C was obtained.

Example 3

Intermediate D

To a solution of C (10.64 g) in methylene chloride (40 mL) was added triethylamine (15.75 mL), p-toluenesulfonyl chloride (11.86 g), and dimethylaminopyridine (690 mg). The resulting suspension was allowed to stir until reaction was complete as determined by TLC then quenched via water work-up with methylene chloride extraction. After purification by silica chromatography, 18.7 g of D was obtained.

Example 4

Intermediate E

To a solution of D (18.7 g) in 200 mL of acetone was added sodium iodide (24.6 g). The mixture heated at reflux for 1½ hours, the solvent removed under reduced pressure and the residue partitioned between water and hexane. The organic layer was separated, dried (sodium sulfate), and the solvent removed. Chromatography (silica) gave 15.4 g of E as a colorless liquid.

Example 5

Intermediate F

This compound was prepared by the method of Christ et al., European Patent Application 92309057.5.

Example 6

Intermediate G

To a solution of 18.6 g of intermediate F and 15.4 g of intermediate E in hexane was added 23.9 g of silver oxide and the mixture refluxed overnight. The mixture was cooled, filtered through diatomaceous earth, the solvent removed, and the residue chromatographed (silica) to give intermediate G (21 g) as a colorless syrup.

Example 7

Intermediate H

To a cold (0° C.) solution of intermediate G (21 g) in methylene chloride was added dropwise 3.5 mL of 48% tetrafluoroboric acid. After 5 minutes, the mixture was washed with aqueous sodium bicarbonate solution and with brine. The mixture was concentrated under reduced pressure and chromatographed (silica) to give intermediate H, 18.7 g, as a colorless syrup.

Example 8

Intermediate I

To a solution of intermediate H (17.6 g) in neat methyl iodide (105 mL) was added silver oxide (83 g). The mixture was stirred overnight and then diluted with hexane and filtered through diatomaceous earth. The mixture was concentrated under reduced pressure and the residue dissolved in methylene chloride (40 mL). The mixture was cooled to 0° C. and to it was added imidazole (2.44 g) and t-butyldimethylsilyl chloride (4.7 mL). It was stirred overnight and 150 mL of sodium bicarbonate solution was added. The organic layer was dried (sodium sulfate) and chromatographed (silica) to give intermediate I, 10.5 g, as a colorless syrup.

Example 9

Intermediate J

Intermediate I was dissolved in 100 mL of methylene chloride to which was added diallyldiisopropylphosphoramidite (7.4 mL), followed by tetrazole (6.37 g). The mixture was cooled and stirred for 20 minutes. A suspension of meta-chloroperoxybenzoic acid (24.2 mmol) in 50 mL of methylene chloride was added over 15 minutes while the temperature of the reaction was maintained below −60° C. Sodium bicarbonate solution was added, the organic layer was separated and dried (sodium sulfate), and the solvent was removed under reduced pressure. Chromatography (silica) gave 14 g of a colorless syrup of intermediate J.

Example 10

Intermediate K

To a suspension of 39.5 g of di(thiophenyl)tin (prepared by the method of Christ et al., European patent application 92309057.5) in 235 mL of methylene chloride was added thiophenol (12 mL). To this mixture was added triethylamine dropwise over 15 minutes. A portion (150 mL) of this "tin reagent" mixture was added dropwise over 15 minutes to a solution of intermediate J (12.9 g) in 25 mL of methylene chloride. The remainder of the "tin reagent" was added over 30 minutes to drive the reaction to completion. The mixture was diluted with ethyl acetate and washed with aqueous 1 N sodium hydroxide and with brine. The organic layer was dried (sodium sulfate), the solvent removed, and the residue chromatographed to give 11.1 g of a yellow syrup, intermediate K.

Example 11

Intermediate L

To a cold solution of intermediate K (11.1 g) and pyridine (7.1 mL) in 80 mL of methylene chloride was added trichloroethyl chloroformate (2.9 mL), and the mixture was stirred overnight. Aqueous sodium bicarbonate solution was added, the organic layer was separated, dried (sodium sulfate), and the solvent removed under reduced pressure. Chromatography gave intermediate L, 12.96 g, as light yellow solid.

Example 12

Intermediate M

Intermediate L, 12.96 g, was dissolved in methylene chloride. To this mixture was added a 6 M solution of hydrogen fluoride in acetonitrile and the mixture stirred for 4 hours. Aqueous sodium bicarbonate solution was added the organic layer separated, dried (sodium sulfate), and the solvent removed under reduced pressure. Chromatography gave 10.9 g of an amber syrup, intermediate M.

Example 13

Intermediate N

To a solution of intermediate M (9.5 g) in 50 mL of trichlororacetonitrile was added potassium carbonate (15 g) and the mixture stirred for 10 minutes. The mixture was filtered through diatomaceous earth and the solvent removed under reduced pressure. Chromatography gave 14.5 g intermediate N, which was used at once in Example 19.

Example 14

Intermediate O

To a solution of intermediate F (160 g) in hexane (475 mL) and iodododecane (474 mL) was added silver oxide (723 g). The mixture was heated at 70° C. in the dark for 2 hours and filtered through diatomaceous earth. The solution was concentrated under reduced pressure and the residue chromatographed to give 221 g of intermediate O as a colorless oil.

Example 15

Intermediate P

To a solution of intermediate O (30 g) in methylene chloride (90 mL) and acetonitrile (90 mL) was added a solution of 48% aqueous hydrogen fluoride (9 mL) in acetonitrile (81 mL). The mixture was stirred for 30 minutes and 350 mL of aqueous sodium bicarbonate was added. The mixture was extracted with methylene chloride. The organic layer was dried (sodium sulfate), the solvent removed under reduced pressure and the residue chromatographed to yield 30 g of intermediate P as a yellow oil.

Example 16

Intermediate Q

To a cold (0° C.) solution of intermediate P (30 g) and imidazole (10.2 g) in methylene chloride (500 mL) was added t-butyldimethylsilyl chloride (10.85 g). The mixture was stirred for 1½ hours and then poured onto 400 mL of saturated aqueous ammonium chloride. The organic layer was separated, dried (sodium sulfate), the solvent removed under reduced pressure, and the residue chromatographed to give 34.5 g of intermediate Q as a colorless syrup.

Example 17

Intermediate R

To a cold (0° C.) solution of intermediate Q (32.2 g) and pyridine (184. mL) in toluene (213 mL) was added a 1.94 M solution of phosgene in toluene. After 20 minutes, allyl alcohol (31 mL) was added, and the mixture stirred for 30 minutes. Aqueous sodium bicarbonate was added, the organic layer was separated and dried (sodium sulfate), and the solvent was removed under reduced pressure. Chromatography gave 36.9 g of intermediate R as a colorless syrup.

Example 18

Intermediate S

To a solution of 2.4 mL of 48% aqueous hydrogen fluoride in 48 mL of acetonitrile was added a solution of intermediate R (20 g) in methylene chloride (24 mL) and the mixture stirred overnight. Aqueous sodium bicarbonate solution was added, the organic layer was separated and dried (sodium sulfate), and the solvent was removed under reduced pressure. Chromatography yielded 11 g of intermediate S as a colorless syrup.

Example 19

Intermediate T

Intermediate S (8.97 g) and intermediate N (14.5 g) were dissolved in toluene (20 mL) and the mixture dried by azeotropic removal of the solvent. This procedure was repeated three times. The dried mixture was dissolved in 50 mL of methylene chloride, which was slowly added to a solution of silver triflate (5.8 g) in 50 mL of methylene chloride. The mixture was stirred for 10 minutes and 250 mL of aqueous sodium bicarbonate solution and 250 mL of 10% aqueous sodium thiosulfate was added. The organic layer was separated, dried (sodium sulfate), and the solvent was removed under reduced pressure. Chromatography gave 13 g of intermediate T as a pale yellow syrup.

Example 20

Intermediate U

To a solution of intermediate T in methylene chloride (10 mL) was slowly added tin(II)tris-benzenethiolate triethylamine complex (12 mL of a 0.5 M solution in methylene chloride). After 10 minutes, an additional equivalent of tin reagent was added. After an additional 15 minutes, an additional equivalent was added. After 15 minutes, ethyl acetate (250 mL) was added and the mixture extracted with 1 N aqueous sodium hydroxide solution (250 mL). The mixture was dried (sodium sulfate) and concentrated under reduced pressure. Toluene was added and the solvent removed under reduced pressure to give an oil, which was used in the next transformation without further purification.

Example 21

Intermediate V

To a cooled (0° C.) solution of intermediate U (2 mmol) in methylene chloride (5 mL) was added 3-ketotetradecanoic acid (997 mg), prepared by the method of Christ et al., European patent application 92309057.5, followed by 1-(3-dimethylaminopropyl)-3-ethylcarbodiimide hydrochloride (1.5 g), and the mixture was stirred for approximately 30 minutes. The mixture was diluted with methylene chloride (150 mL), washed with 1 N aqueous sodium hydroxide, dried (sodium sulfate) and the solvent removed under reduced pressure. Chromatography on silica followed by chromatography on basic alumina gave 1.64 g of intermediate V.

Example 22

Intermediate W

A solution of intermediate V (1.45 g) in glacial acetic acid (5 mL) was added to a suspension of well-stirred zinc copper couple (14 g) in acetic acid (10 mL). The mixture was stirred for 15 minutes and additional zinc/copper couple (10 g) was added. After an additional 15 minutes, the mixture was filtered through diatomaceous earth, which was then washed with ethyl acetate. The combined washings were diluted with toluene and the solvent removed under reduced pressure. The residue was chromatographed on a bilayered mixture of basic alumina and silica to give intermediate W, which was used without further purification.

Example 23

Intermediate X

A solution of intermediate W (1.02 mmol) and cis-vaccenic acid (575 mg) was dissolved in toluene (5 mL) three times and the solvent removed under reduced pressure. The dried residue was dissolved in methylene chloride (3 mL) and 1-(3-dimethylaminopropyl)-3-ethylcarbodiimide hydrochloride (780 mg) was added and the mixture stirred for 3 hours. The mixture was diluted with methylene chloride and chromatographed directly to give 734 mg of intermediate X. Further chromatography of the impure fractions gave an additional 58 mg of material.

Example 24

Intermediate Y

To a solution of intermediate X (785 mg) in methylene chloride (10 mL) was added a solution of 48% aqueous hydrogen fluoride in acetonitrile (15 mL). The mixture was stirred for 90 minutes, diluted with methylene chloride (50 mL), and washed with water and aqueous sodium bicarbonate solution. The mixture was dried (sodium sulfate) and chromatographed to give intermediate Y, 719 mg.

Example 25

Intermediate Z

Intermediate Y (719 mg) was dissolved in methylene chloride and sodium sulfate (1.4 g) was added. Diallyldiisopropylphosphoramidite (189 µL) and tetrazole (162 mg) were added, the mixture stirred for 10 minutes and then cooled to −78° C. A solution of m-chloroperoxybenzoic acid (192 mg) in methylene chloride (4 mL) was added dropwise. The mixture was washed with aqueous sodium thiosulfate and aqueous sodium bicarbonate, was dried (sodium sulfate), and the solvent was removed under reduced pressure. The residue was chromatographed to give 660 mg of intermediate Z.

Example 26

Compound 1

To a solution of tetrakis(triphenylphosphine)palladium (0) (166 mg) in 2 mL of tetrahydrofuran: acetic acid (10:1) mixture was added a solution of intermediate Z (660 mg) in 3 mL of the same solvent mixture. After 30 minutes, additional tetrakis(triphenylphosphine)palladium (0) was added. After an additional 1½ hours, toluene was added, and the solvent removed under reduced pressure. The mixture was purified by chromatography on diethylaminoethylcellulose. The purified mixture was dissolved in 0.1 N aqueous sodium hydroxide, filtered through a 0.45 μm sterile filter, and purified by HPLC on a YMC-Pack ODS-AP column to give 130 mg of compound 1.

Analytical data for some of the compounds and intermediates made by the methods described above is given below:

Compound 1: $^1$H NMR (CD$_3$OD) δ: 5.3 (1H, m), 4.6 (1, m), 4.0 (m, m), 3.9 (1H, d), 3.7 (1H, t), 3.6 (1H, t), 3.4 (3H, s), 3.3 (3H, t), 2.6 (2H, t), 2.3 (2H, m), 2.0 (2H, m), 1.7–1.2 (m, m), 0.9 (6H, t).

$^{31}$P NMR (CD$_3$OD) δ: 4.71, 3.98.

Compound 1: (M+Na)$^+$=1333
Compound 2: (M+3 Na)$^+$=1363
Compound 3: (M+3 Na)$^+$=1365
Compound 5: (M+Na)$^+$=1303
Compound 6: (M+Na)$^+$=1359
Compound 7: (M+Na)$^+$=1305
Compound 8: (M+3 Na)$^+$=1393
Compound 10: (M+Na)$^+$=1425

Intermediate G: $^1$H NMR (CDCl$_3$) δ: d, (1H), 3.9–3.7 (m, multiple), 3.65 (t, 1 H), 3.37 (s,3H), 3.2 (m,2H), 1.75 (q, 2H), 1.52 (s,3H), 1.4 (s,3H), 1.3 (broad m, multiple), 0.95 (s,9H), 0.9 (t,3H), and 0.2 (d,6H)

Intermediate H: $^1$H NMR (CDCl$_3$) δ:4.58 (d,1H), 4.09 (m,2H), 3.9 (dd,1H), 3.75 (dd,1H), 3.7 (m,1H), 3.5 (t,1H), 3.37 (s,3H), 3.23 (t,1H), 3.05 (t,1H), 1.8 (m,2H), 1.68 (m,1H), 1.5 (m,1H), 1.3 (broad m, multiple), 0.95 (s,9H), 0.9 (t,3H), 0.2 (d,6H)

Intermediate I:$^1$H NMR (CDCl$_3$) δ:4,52 (d,1H), 4.05 (m,2H), 3.75 (m,1H), 3.67 (t,1H), 3.5 (t,1H), 3.45 (s,3H), 3.35 (s,3H), 3.25 (t,1H), 3.05 (t,1H), 1.8 (m,2H), 1.65 (m, 1H), 1.5 (m,1H), 1.3 (broad s,m), 0.95 (s,9H), 0.9 (t,3H), 0.2 (s,6H)

Intermediate J: $^1$H NMR (CDCl$_3$) δ: 5.95 (m,2H), 5.35 (d,1H), 5.22 (d,1H), 4.6 (q,2H), 4.5 (d,1H), 4.32 (q,1H), 3.9–3.75 (m,3H), 3.7 (dd,1H), 3.65 (dd,1H), 3.45 (m,1H), 3.38 (s,3H), 3.33 (s,3H), 3.27 (t,1H), 3.2 (t,1H), 1.9–1.75 (m,3H), 1.5 (m,1H), 1.3 (broad m,multiple), 0.95 (s,9H), 0.9 (t,3H), 0.2 (s,6H)

Intermediate L: $^1$H NMR (CDCl$_3$) δ:5.95 (d,1H), 5.4 (d,2H), 5.25 Z(d,2H), 4.95 (d,1H), 4.7 (q,2H), 4.55 (q,2H), 4.32 (q,1H), 3.9–3.75 (m,3H), 3.7 (dd,1H), 3.65 (dd,1H), 3.55 (m,1H), 3.4 (m,1H), 3.4 (s,3H), 3.3 (s,3H), 3.25 (m,1 H), 1.75 (m,multiple), 1.5–1.4 (m,2H), 1.3 (broad s,multiple), 0.95–0.9 (broad s,12H), 0.2 (d,6H)

Intermediate M: $^1$H NMR (CDCl$_3$) δ: 5.95 (m,2H), 5.75 (d,1H), 5.4 (d,1H), 5.25 (d,2H), 4.75–4.65 (dd,2H), 4.6 (q,1H), 4.3 (q,1H), 4.1 (m,2H), 3.9 (m,2H), 3.65 (m,1H), 3.4 (s,3H), 3.25 (s,3H), 1.75 (broad m,2H), 1.55–1.4 (m,2H), 1.3 (broad s,multiple), 0.9 (t,3H)

Intermediate O; $^1$H NMR (CDCl$_3$) δ: 4.5 (d,1H), 3.8 (dd,1H), 3.78 (m,2H), 3.6 (m,multiple), 3.2 (m,2H), 1.5 (s,3H), 1.4 (s,3H), 1.3 (broad s, multiple), 0.95 (s,9H), 0.9 (t,3H), 0.18 (d,6H)

Intermediate P: $^1$H NMR (CDCl$_3$) δ:4.5 (d,1H), 3.75 (dd,2H), 3.6 (q,2H), 3.5 (t,1H), 3.3 (m,1H), 3.2 (t,1H), 3.0 (t,1H), 1.6 (m,2H), 1.25 (broad s,multiple), 0.95 (s,9H), 0.9 (t,3H), 0.18 (d,6H)

Intermediate Q: $^1$H NMR (CDCl$_3$) δ: 4.5 (d,1H), 3.82 (t,2H), 3.7 (m,2H), 3.6 (t,1H), 3.3 (m,1H), 3.2 (t,1H), 3.05 (q,2H), 1.6 (m,2H), 1.3 (broad s,multiple), 0.95 (s,9H), 0.88 (s,9H), 0.85 (t,3H), 0.2 (d,6H), 0.1 (d,6H)

Intermediate R: $^1$H NMR (CDCl$_3$) δ: 5.9 (m,1H), 5,4–5.25 (dd,2H), 4.75 (t,1H), 4.6 (d,2H), 4.45 (d,1H), 3.75 (q,1H), 3.7 (d,2H), 3.53 (q,1H), 3.38 (m,1H), 3.25 (t,1H), 3.15 (t,1H), 1.5 (t,2H), 1.25 (s, multiple), 0.95(s,9H), 0.85 (m,12H), 0.2 (s,6H), 0.07 (s,6H)

Intermediate S: $^1$H NMR (CDCl$_3$) δ: 5.9 (m,1H), 5.4–5.25 (dd,2H), 4.75 (t,1H), 4.6 (d,2H), 4.52 (d,1H), 3.7 (m,multiple), 3.65–3.6 (dd,2H), 3.55 (q,1H), 3.4 (m,1H), 3.28 (t,1H), 3.2 (t,1H), 1.5 (t,2H), 1.3 (s, multiple), 0.9 (s,9H), 0.85 (t,3H), 0.2 (s,6H)

Intermediate T: $^1$H NMR (CDCl$_3$) δ: 5.9 (m,3H), 5.6 (d,1H), 5.4–5.2 (m,6H), 4.8 (d,1H), 4.7–4.6 (m,2H), 4.55 (q,1H), 4.5 (d,1H), 4.3 q,1H), 3.8–3.7 (m,multiple), 3.6 (dd, 1H), 3.5 (m,multiple), 3.35 (s,3H), 3.2 (s,3H), 3.15 (t,1H), 1.7 (m,2H), 1.5 (m,2H), 1.3 (s,multiple), 0.95 (t,6H), 0.2 (t,6H)

Intermediate V: $^1$H NMR (CDCl$_3$) δ:7.3 (d,1H), 5.95 (m,3H), 5.6 (d,1H), 5.4–5.2 (m,6H), 4.95 (d,1H), 4.8 (d,1H), 4.7–4.5 (m,multiple)4.3 (q,1H), 3.9–3.65 (m,multiple), 3.6 (m,multiple), 3.45 (t,1H), 3.4 (t,3H), 3.35 (s,2H), 3.28 (3H), 2.5 (t,2H), 1.8 (m,2H), 1.6 (m,2H), 1.45 (m,2H), 1.3 (broad s,multiple), 0.95–0.8 (m,18H), 0.15 (d,6H)

Intermediate X: $^1$H NMR (CDCl$_3$) δ:7.3 (d,1H), 5.95 (m,4H), 5.4–5.2 (m,8H), 4.95 (d,1H), 4.8 (d,1H), 4.7 (t,1H), 4.6 (d,1H), 4.55 (q,1H), 4.3 (q,1H), 4.1 (t,1H), 3.9 (q,1H), 3.8 (t,1H), 3.7–3.5 (m,multiple), 3.45 (t,1H), 3.35 (s,3H), 3.3 (s,2H), 3.28 (s,3H), 2.5 (t,2H), 2.2 (t,1H), 2 (d,1H), 1.7 (q,2H), 1.6 (m,2H), 1.3 (s,multiple), 0.95–0.8 (m,21), 0.15 (d,6H)

Intermediate Y: $^1$H NMR (CDCl$_3$) δ: 6.65 (d,1H), 6.55 (d,1H), 5.905 (m,5H), 5.7 (m,1H), 5.4–5.2 (m,12H). 4.8 (m,2H), 4.6 (d,1H), 4.5 (m,10H), 4.3 (q,1H), 4.1 (m,1H), 3.85–3.45 (m,multiple), 3.4 (s,3H), 3.35 (s,3H), 3.25 (s,3H), 3.2 (t,1H), 2.5 (dd,2H), 2.2 (t,2H), 2 (m,mutiple), 1.7–1.2 (m,mutiple), 0.9 (t,12H).

BIOLOGICAL EXAMPLES

Both bacterial LPS and bacterial lipid A elicit production of tumor necrosis factor (TNF), IL-1β, IL-6, and IL-8, as well as other cytokines and cellular mediators in human whole blood and in a human macrophage cell lines. Generation of pathophysiological quantities of these cytokines has been found to play an important part in the initiation of the systemic inflammatory response syndrome and septic shock. The liposaccharide analogs described herein inhibit such LPS- and/or lipid A-mediated induction of cytokines as demonstrated by the following experiments.

Example A

In Vitro Inhibition of LPS-Induced Production of Cytokines

Whole human blood was prepared and tested as described (Rose et al., Infection and Immunity, 63:833–839, 1995). HL-60 cells were cultured in RPMI medium supplemented with 10% fetal calf serum and antibiotics, and induced to differentiate into macrophages by treatment with 0.1 μM 1,25-dihydroxycholecalciferol (Vitamin D3; Biomol Research Laboratories, Plymouth Meeting, Pa.), and tested for LPS mediated generation of IL-8. Briefly, bacterial LPS (e.g., from *E. coli* 0111:B4; Sigma Chemicals, St. Louis, Mo.) at 10 ng/mL or lipid A (Daiichi Chemicals, Tokyo, Japan) were added as 10-fold concentrated solutions in Ca$^{++}$, Mg$^{++}$ free Hank's balanced salt solution (CMF-HBSS; Gibco). In experiments involving analogs of the present invention, the analog was added immediately before addition of LPS or lipid A in CMF-HBSS (e.g., between 0 and 100 µM as a 10× concentrated aliquot). Following incubation of three hours, plasma was prepared from whole blood, or culture supernatant was removed and assayed for the presence of the indicated cytokine using an ELISA assay kit from Genzyme (Cambridge, Mass.), following the instructions of the manufacturer, however, any other standard ELISA kits may be utilized. Experiments were performed in triplicate at least twice.

The lipid A analogs inhibited LPS-induced production of TNF in human whole blood in a concentration-dependent manner. Of the analogs tested, Compound 1 was found to be one of the most effective compounds. The results of this test are as shown in FIG. 1. Compound 1 inhibits LPS-induced production of TNF, exhibiting an $IC_{50}$ of approximately 1.5 nM. Other analogs found to inhibit LPS-induced TNF production included compound 2, compound 3, compound 4, compound 5, compound 6, compound 7, compound 8, compound 9, and compound 10. These compounds exhibited $IC_{50}$s of between 1.5 nM and 159 nM.

Compound 1 also inhibited LPS-mediated induction of IL-8 in HL-60 (human macrophage-like) cells. Inhibition of IL-8 generation was complete at concentrations of 1 nM and greater Compound 1 when either LPS or lipid A was used as agonist.

Compounds of this invention similarly inhibited the LPS-induced production of other cytokines in human whole blood, even though some of these cytokines were generated several hours after addition of LPS. For instance, IL-1β and IL-6 require four or more hours for maximum levels to be reached, while IL-8 reaches maximum levels ten or more hours after LPS addition. Using methods described above, compounds of this invention were added at concentrations between 0 and 10 µM, and LPS was added at 10 ng/mL. Inhibition of production of TNF, IL-1β, IL-6, and IL-8 was measured as a function of time after addition of LPS. This inhibition of cytokine generation was also found to be concentration dependent, but in all cases, suppression of all cytokine synthesis was >90% at compound 1 concentrations of 10 nM and more for up to 24 hours after addition of LPS.

Example B

Persistence of Compounds in Human Whole Blood

Figure 2:
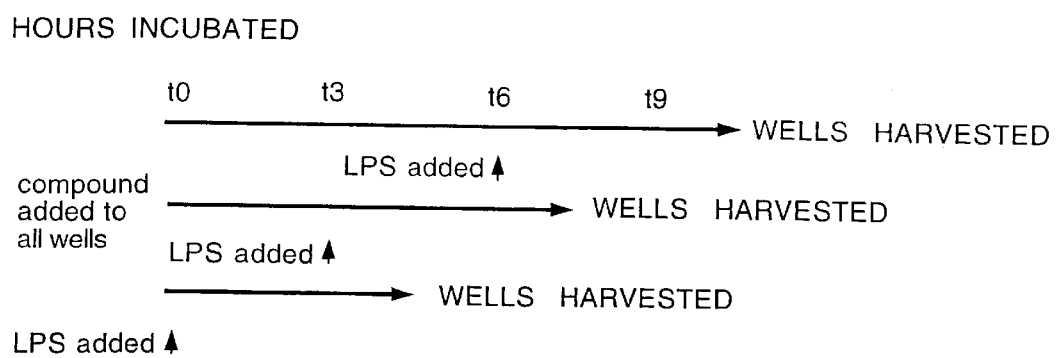
FIG. 2 depicts the general scheme used to analyze antagonistic efficacy of drug after incubation in whole blood for various times.

Although some of the compounds of this invention are not rapidly removed from the circulation, their activity diminishes with a half-life of 1–3 hours. To maintain antagonistic efficacy, this rapid deactivation may require continuous administration. The study of this deactivation has led to the development of an assay to measure in vitro deactivation of drugs in human whole blood. This is done by preincubating lipid A antagonists with blood for various periods of time followed by addition of the LPS "challenge," as is described above, incubation for three hours, and assay for released cytokines. A schematic for this assay is shown in FIG. 2.

Figure 3:
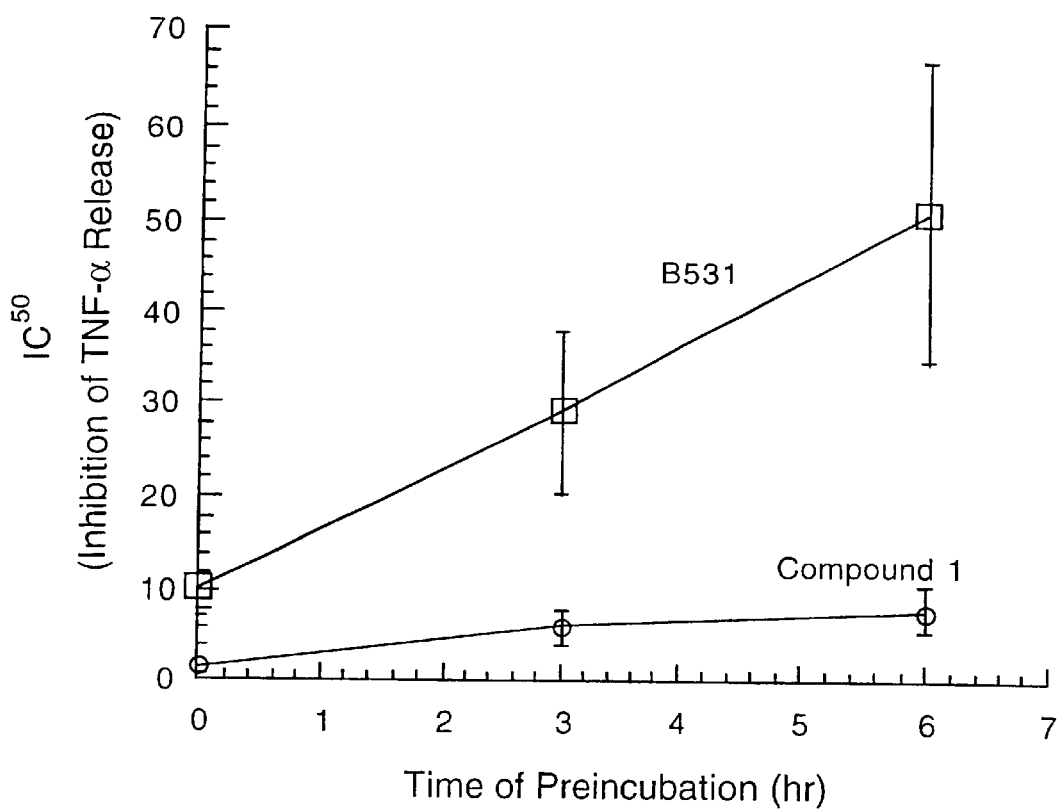
FIG. 3 depicts the relationship between time versus ability of the test compound to inhibit TNF-α and demonstrates that Compound 1 has a superior duration of action as an LPS antagonist than does B531. These data are the average of 7 separate experiments, each run in triplicate.

Using this assay, it can be demonstrated that B531, as described by Christ et al., U.S. Pat. No. 5,530,113, "deactivates" (i.e., loses activity with increasing time of preincubation). As is shown in FIG. 3, compound 1 also deactivates, but its superior activity and decreased deactivation rate make it as active after 6 hours as B531 was just after its addition. These data are the average of 7 separate experiments run in triplicate.

Example C

Inhibition of TNF or IL-6 Production in in vitro Animal Model Systems

LPS-induced TNF or IL-6 production was inhibited by compounds of the present invention in whole blood or macrophages isolated from guinea pigs, rats and mice. Hartley-White guinea pig (Elm Hill Breeders, Chelmsford, Mass.) and C57BL/6 mouse (Jackson Labs, Bar Harbor, Me.) macrophages were isolated from the abdomen of primed animals. Priming was accomplished by intraperitoneal injection of 2 mg of Bacillus calmette guerin (BCG; RIBI Immunochemical Research, Inc., Hamilton, Mont.) at a concentration of 10 mg/mL in physiological saline for mice and 2 mg of BCG at a concentration of 2 mg/7 mL in mineral oil for guinea pigs. Three days post-injection, peritoneal macrophages were isolated from the abdomen of the animals by standard techniques. Cells were allowed to adhere to culture plates for two to three hours, and were then cultured with RPMI 1640 medium containing 10% fetal calf serum, and LPS (final concentration of 10 ng/mL) was added as is described above. To test inhibition, compounds of this invention (at a concentration of between 0 and 100 µM) were added to the culture medium just prior to LPS addition. Following a three-hour incubation period, guinea pig, mouse, and rat TNF levels and/or IL-6 levels were assayed by ELISA, or by the cytolytic bioassay described in Lymphokines 2:235, 1981 for TNF released from guinea pig macrophages. In mouse peritoneal macrophages, Compound 1 provided effective inhibition ($IC_{50}$=16 nM for IL-6 and 20 nM for TNF, respectively); in guinea pig macrophages, the $IC_{50}$ for TNF release was 0.3 nM; and in rat peritoneal macrophages, the $IC_{50}$ for release of TNF was 11 nM.

Example D

In Vivo Assays

BCG-primed mice (Vogel et al., J. Immunology 124:2004–2009, 1980) were utilized as an in vivo assay system for monitoring the inhibitory effects of lipid A analogs on (1) LPS-induced TNF production and (2) LPS-induced lethality as follows.

Five week-old male C57BL/6 mice (supra) were primed by intravenous tail vein injection with 2 mg of BCG. Ten days post-injection, E. coli LPS (supra) in pyrogen-free 5% glucose solution (Otsuka Pharmaceuticals Inc., Tokyo, Japan) was administered intravenously through the tail vein of the BCG-primed mice. LPS was administered at 1–3 µg/mouse for both TNF production and mortality studies. The test compound was administered as a component of the injected LPS solution at a concentration of between 3 and 300 µg/mouse. Plasma was obtained one hour post LPS injection, and TNF was assayed by the ELISA assay described above. Mortality resulting from septic shock was recorded for 36 hours after LPS injection.

Compounds of this invention effectively suppressed the production of TNF following administration of LPS. Compound 10 and Compound 1 effectively inhibited TNF production in vivo in mice ($ED_{50s}$=5 and 10.6 µg/mouse, respectively). Compound 2, compound 3, compound 4, compound 5, compound 6, compound 7, compound 8, and compound 9 also inhibited TNF production with $ED_{50}$s between 10 and 200 µg/mouse with compounds 5, 6, and 7 giving $ED_{50}$ values >100.

In parallel experiments carried out in guinea pigs, these analogs were also effective inhibitors of LPS-induced TNF production in vivo (optimum $ED_{50}$s between 2.3 and 6.1 µg/guinea pig for compound 1, compound 7, and compound 10.

All of the above-mentioned patents and other publications are hereby incorporated by reference.

What is claimed is:

1. A pharmaceutical composition comprising an antiendotoxin compound having the formula:

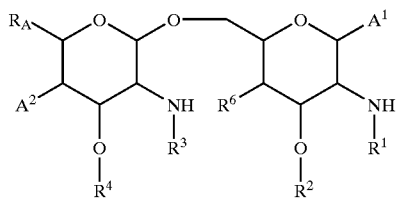

where $R^1$ is selected from the group consisting of

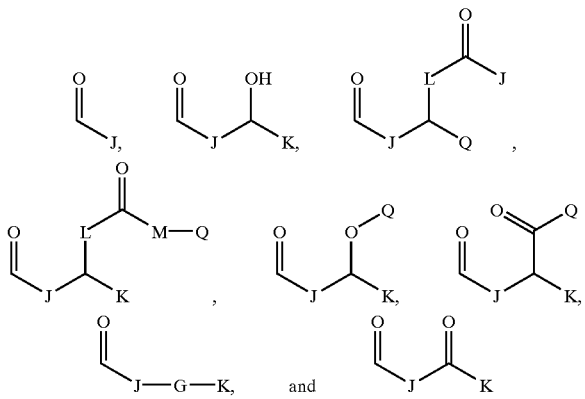

and 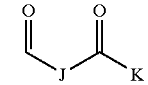 where each J, K, and Q, independently, is straight or branched C1 to C15 alkyl; L is O, NH, or CH2; M is O or NH; and G is NH, O, S, SO, or $SO_2$;

$R^2$ is straight or branched C5 to C15 alkyl;

$R^3$ is selected from the group consisting of straight or branched C5 to C18 alkyl,

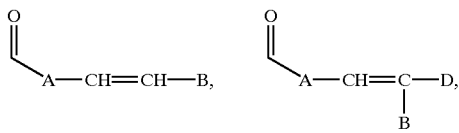

-continued 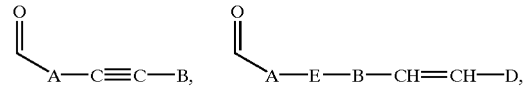 and

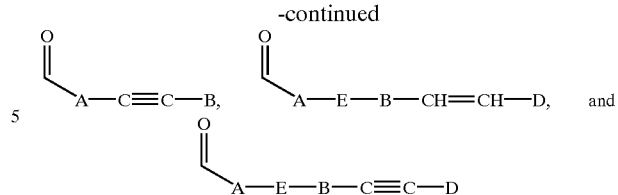

where E is NH, O, S, SO, or $SO_2$; each A, B, and D, independently, is straight or branched C1 to C15 alkyl;

$R^4$ is selected from the group consisting of straight or branched C4 to C20 alkyl, and

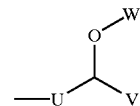

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J', —J'—OH, —J'—O—K', —J'—O—K'—OH, and —J'—O—$PO(OH)_2$, where each J' and K', independently, is straight or branched C1 to C5 alkyl;

$R^6$ is selected from the group consisting of hydroxy, halogen, C1 to C5 alkoxy, and C1 to C5 acyloxy, $A^1$ and $A^2$, independently, are selected from the group consisting of

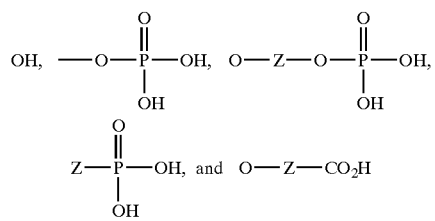

and where Z is straight or branched C1 to C10 alkyl;

or pharmaceutically acceptable salts thereof, in a nebulized formulation.

2. The composition of claim 1, wherein said Lipid A analog has the structure:

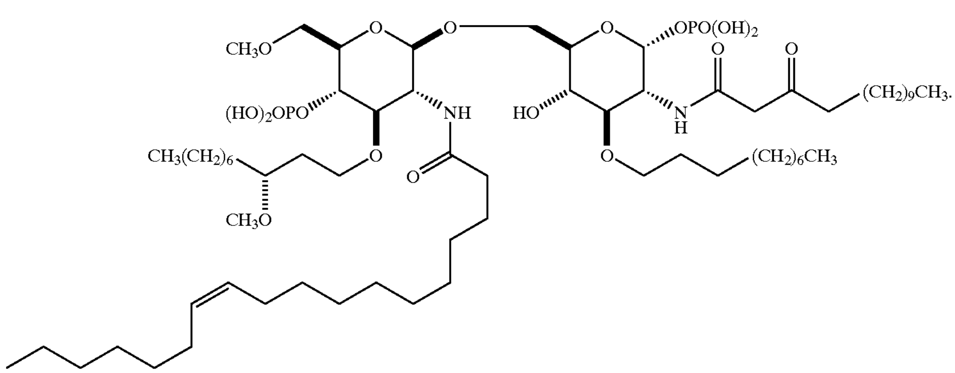

3. A pharmaceutical composition comprising an antiendotoxin compound having the formula:

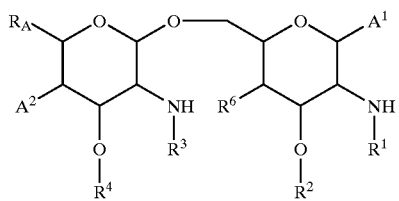

$R^1$ is selected from the group consisting of

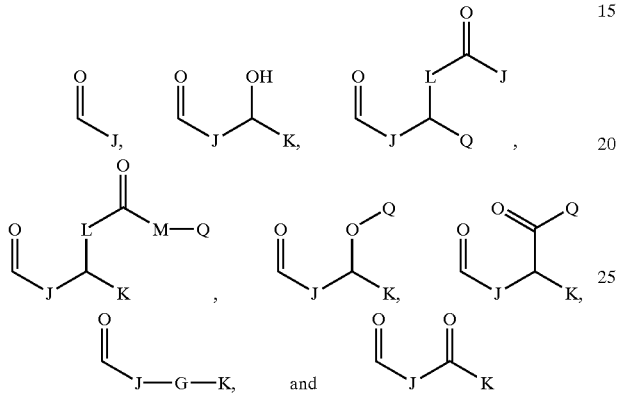

where each J, K and Q, independently, is straight or branched C1 to C15 alkyl; L is O, NH, or CH₂; M is O or NH; and G is NH, O, S, SO, or SO₂;

$R^2$ is straight or branched C5 to C15 alkyl;

$R^3$ is selected from the group consisting of straight or branched C5 to C18 alkyl,

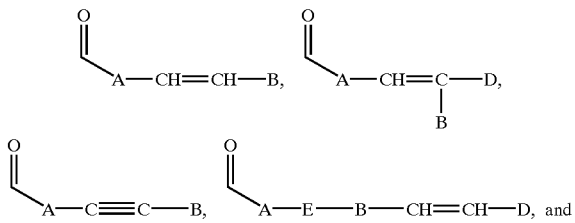

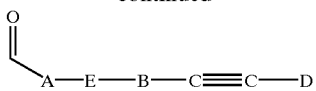

where E is NH, O, S, SO, or SO₂; each A, B, and D, independently, is straight or branched C1 to C15 alkyl;

$R^4$ is selected from the group consisting of straight or branched C4 to C20 alkyl, and

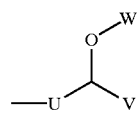

where each U and V, independently, is straight or branched C2 to C15 alkyl and W is hydrogen or straight or branched C1 to C5 alkyl;

$R_A$ is $R^5$ or R5—O—CH₂—, $R^5$ being selected from the group consisting of hydrogen, J', —J'—OH, —J'—O—K', —J'—O—K'—OH, and —J'—O—PO(OH)₂, where each J' and K', independently, is straight or branched C1 to C5 alkyl;

$R^6$ is selected from the group consisting of hydroxy, halogen, C1 to C5 alkoxy, and C1 to C5 acyloxy;

$A^1$ and $A^2$, independently, are selected from the group consisting of

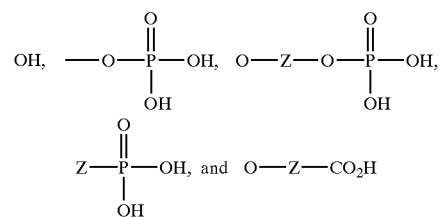

where Z is straight or branched C1 to C10 alkyl;

or pharmaceutically acceptable salts thereof, in an aerosolized formulation.

4. The composition of claim 3, wherein said Lipid